United States Patent
Lu et al.

(10) Patent No.: US 11,939,391 B2
(45) Date of Patent: Mar. 26, 2024

(54) ANTI-TfR1 ANTIBODY MAb11-22.1 CONJUGATES FOR CANCER TREATMENT

(71) Applicant: MedAbome, Inc., Fremont, CA (US)

(72) Inventors: Mason Lu, Fremont, CA (US); Qinhong Ma, Fremont, CA (US)

(73) Assignee: MEDABOME, INC., Fremont, CA (US)

( * ) Notice: Subject to any disclaimer, the term of this patent is extended or adjusted under 35 U.S.C. 154(b) by 256 days.

(21) Appl. No.: 17/542,948

(22) Filed: Dec. 6, 2021

(65) Prior Publication Data
US 2023/0174663 A1    Jun. 8, 2023

(51) Int. Cl.
*C07K 16/28*    (2006.01)
*A61K 35/17*    (2015.01)

(52) U.S. Cl.
CPC .......... *C07K 16/2896* (2013.01); *A61K 35/17* (2013.01); *C07K 16/2863* (2013.01); *C07K 2317/52* (2013.01); *C07K 2317/565* (2013.01); *C07K 2317/622* (2013.01); *C07K 2319/03* (2013.01)

(58) Field of Classification Search
None
See application file for complete search history.

(56) References Cited

U.S. PATENT DOCUMENTS

2015/0197574 A1*   7/2015   Cruz-Moura .......... A61P 43/00
                                                                                                  424/143.1

OTHER PUBLICATIONS

Lloyd et al (Protein Engineering, Design & Selection, 22:159-168, 2009).*
Edwards et al (J Mol Biol, 14;334(1):103-118, 2003).*
Gussow et al (Methods in Enzymology. 1991; 203: 99-121).*
Winkler et al (J. Imm., 265:4505-4514, 2000).*
Muyldermans, Serge (ARB, 82:775-797, 2013).*

* cited by examiner

*Primary Examiner* — Brad Duffy
(74) *Attorney, Agent, or Firm* — Eric P. Mirabel

(57) ABSTRACT

The present invention provides a therapeutic agent for the treatment, prevention and diagnosis of cancers associated with cells that overexpressing transferrin receptor 1 (TfR1) and its variants on the cell surface, including but not limited to AML, ALL, lymphoma, multiple myeloma, breast cancer, gastric cancer, glioblastoma, prostate cancer, urothelial bladder cancer, pancreatic cancer, esophageal cancer, colorectal cancer, ovarian cancer, liver cancer. The agent is based on the amino acid sequences of the novel light chain and heavy chain variable regions of an anti-TfR1 monoclonal antibody (mAb), MAb11-22.1, which, is highly specific for tumor cells and in an ADC form, can functionally inhibit the proliferation of several human cancer cell lines and the growth of AML cell line-derived xenograft tumors in mouse models.

19 Claims, 24 Drawing Sheets
(6 of 24 Drawing Sheet(s) Filed in Color)
Specification includes a Sequence Listing.

Fig. 3B

| Loading | rTfR1-ECD | $K_D$ (M) | $K_D$ Error | $k_{on}$(1/Ms) | $k_{on}$ Error | $k_{off}$(1/s) | $k_{off}$ Error | Full $X^2$ | Full $R^2$ |
|---|---|---|---|---|---|---|---|---|---|
| MAb11-22.1 mAb 50 nM | 20 nM | <1.0E-12 | 2.01E-12 | 6.04E+05 | 9.80E+03 | <1.0E-07 | | 0.7868 | 0.9909 |
| | 8 nM | <1.0E-12 | 2.01E-12 | 6.04E+05 | 9.80E+03 | <1.0E-07 | | 0.7868 | 0.9909 |
| | 3.2 nM | <1.0E-12 | 2.01E-12 | 6.04E+05 | 9.80E+03 | <1.0E-07 | | 0.7868 | 0.9909 |
| | 1.28 nM | <1.0E-12 | 2.01E-12 | 6.04E+05 | 9.80E+03 | <1.0E-07 | | 0.7868 | 0.9909 |
| MAb11-22.1 mAb 10 nM | 20 nM | <1.0E-12 | 1.14E-12 | 1.16E+06 | 2.12E+04 | <1.0E-07 | | 1.035 | 0.989 |
| | 8 nM | <1.0E-12 | 1.14E-12 | 1.16E+06 | 2.12E+04 | <1.0E-07 | | 1.035 | 0.989 |
| | 3.2 nM | <1.0E-12 | 1.14E-12 | 1.16E+06 | 2.12E+04 | <1.0E-07 | | 1.035 | 0.989 |
| | 1.28 nM | <1.0E-12 | 1.14E-12 | 1.16E+06 | 2.12E+04 | <1.0E-07 | | 1.035 | 0.989 |

Fig. 3C

| Loading | Fab* | K$_D$ (M) | K$_D$ Error | k$_{on}$(1/Ms) | k$_{on}$ Error | k$_{off}$ (1/s) | k$_{off}$ Error | Full X^2 | Full R^2 |
|---|---|---|---|---|---|---|---|---|---|
| MAb11-22.1 mAb 50 nM | 300 | 1.45E-09 | 4.43E-11 | 4.17E+04 | 7.00E+02 | 6.03E-05 | 1.55E-06 | 2.8165 | 0.9956 |
| | 100 | 1.45E-09 | 4.43E-11 | 4.17E+04 | 7.00E+02 | 6.03E-05 | 1.55E-06 | 2.8165 | 0.9956 |
| | 33.3 | 1.45E-09 | 4.43E-11 | 4.17E+04 | 7.00E+02 | 6.03E-05 | 1.55E-06 | 2.8165 | 0.9956 |
| MAb11-22.1 mAb 10 nM | 300 | 1.04E-09 | 2.75E-11 | 5.71E+04 | 8.81E+02 | 5.92E-05 | 1.28E-06 | 1.5033 | 0.9957 |
| | 100 | 1.04E-09 | 2.75E-11 | 5.71E+04 | 8.81E+02 | 5.92E-05 | 1.28E-06 | 1.5033 | 0.9957 |
| | 33.3 | 1.04E-09 | 2.75E-11 | 5.71E+04 | 8.81E+02 | 5.92E-05 | 1.28E-06 | 1.5033 | 0.9957 |

* Goat anti-mouse (H+L) Fab

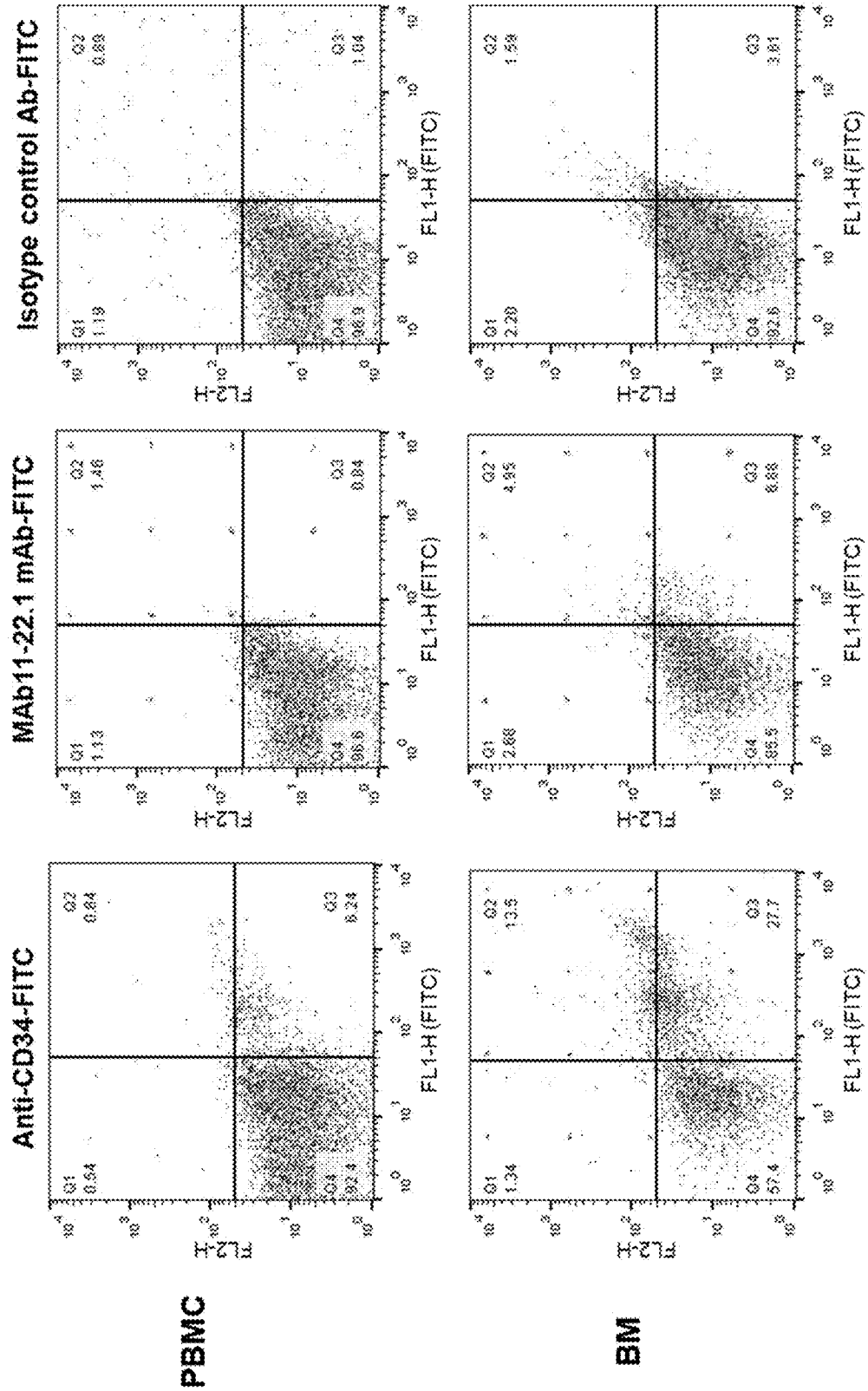

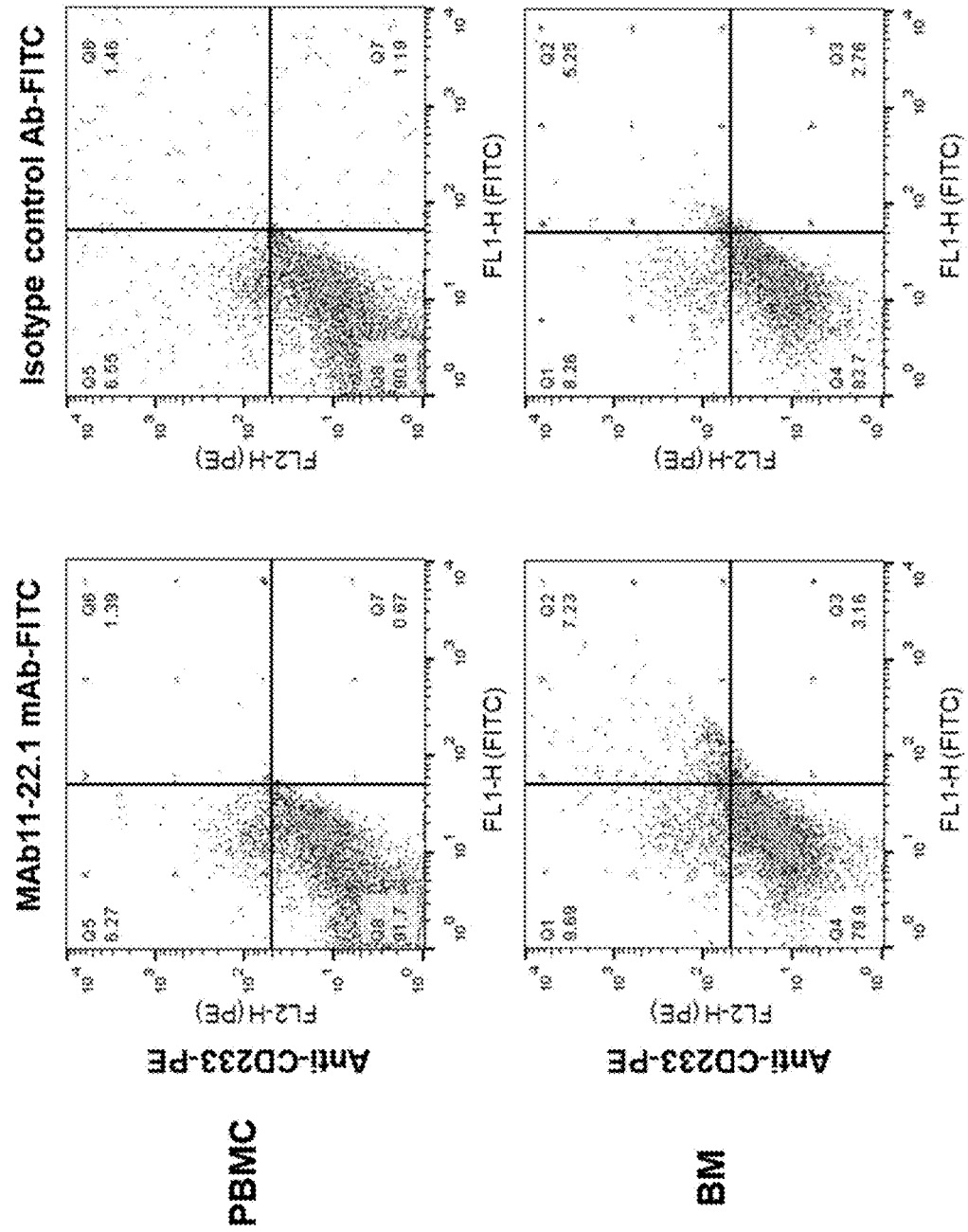

| Loading | Fab* | $K_D$ (M) | $K_D$ Error | $k_{on}$(1/Ms) | $k_{on}$ Error | $k_{off}$ (1/s) | $k_{off}$ Error | Full X^2 | Full R^2 |
|---|---|---|---|---|---|---|---|---|---|
| MAb11-22.1 cAb 50 nM | 300 nM | 2.18E-09 | 2.88E-11 | 3.35E+04 | 3.40E+02 | 7.28E-05 | 6.19E-07 | 14.1253 | 0.9979 |
| | 100 nM | 2.18E-09 | 2.88E-11 | 3.35E+04 | 3.40E+02 | 7.28E-05 | 6.19E-07 | 14.1253 | 0.9979 |
| | 33.3 nM | 2.18E-09 | 2.88E-11 | 3.35E+04 | 3.40E+02 | 7.28E-05 | 6.19E-07 | 14.1253 | 0.9979 |
| | 11.1 nM | 2.18E-09 | 2.88E-11 | 3.35E+04 | 3.40E+02 | 7.28E-05 | 6.19E-07 | 14.1253 | 0.9979 |
| | 3.7 nM | 2.18E-09 | 2.88E-11 | 3.35E+04 | 3.40E+02 | 7.28E-05 | 6.19E-07 | | |

* Goat anti-human (H+L) Fab

ANTI-TfR1 ANTIBODY MAb11-22.1 CONJUGATES FOR CANCER TREATMENT

SEQUENCE LISTING

The instant application contains a Sequence Listing which has been submitted electronically in ASCII format and is hereby incorporated by reference in its entirety. Said ASCII copy, created on Dec. 17, 2021, is named MedAb-ADC_SL.txt and is 7,582 bytes in size.

FIELD OF THE INVENTION

The present invention relates to the use of antibodies to bind and modulate the internalization and activity of transferrin receptor 1 (TfR1) and its isoforms in human cancer cells. The invention also relates to the antibody or its conjugated with small molecule (antibody drug conjugation, ADC) used for in vitro, in situ, and/or in vivo diagnosis and/or treatment of mammalian cells or pathological conditions associated with TfR1 and its isoforms.

BACKGROUND

Transferrin receptor 1 (TfR1, CD71) is a type II transmembrane glycoprotein consisting of 760 amino acids that are linked by two disulfide bonds to form a 180-kDa homodimer that plays a crucial role in the regulation of iron uptake and cell growth (BOMFORD and MUNRO. Hepatology. 5:870-875, 1985). When diferric transferrin (TO binds to TfR1 on cell surface, the holo-Tf-TfR1 complex is internalized via clathrin-coated pits and is delivered into acidic endosomes, where the iron-Tf-TfR1 complex undergoes conformational change triggered by low pH, and iron is subsequently released and transported to the cytosol. The apo-Tf/TfR1 complex is then recycled back to the cell surface where apo-Tf dissociates from the receptor (WARD. Invest Radiol. 22:74-83, 1987; DANIELS et al. Clin Immunol. 121:144-158, 2006). TfR1 expression is increased on rapidly proliferating cells, such as precursors of blood cells, hepatocytes, keratinocytes, in which iron is highly required for heme synthesis, whereas its expression is decreased or absent on nondividing cells. TfR1 is overexpressed in primary and metastatic cancer cells of lymphocytes, pancreas, stomach, colon, lung, breast, bladder, and skin origins (GATTER et al. J Clin Pathol. 36:539-545, 1983; FAULK et al. Lancet. 2:390-392, 1980; SUTHERLAND et al. Proc Natl Acad Sci USA 78:4515-4519, 1981; DANIELS et al. Clin Immunol. 121:144-158, 2006; JEONG et al. Biochem Biophys Res Commun. 471:373-379, 2016; PEER et al. Nat Nanotechnol. 2:751-760, 2007; QIAN et al. Pharmacol Rev. 54:561-587, 2002; RICHARDSON et al. Biochim Biophys Acta Gen Subj. 1790:702-717, 2009). Since cancer cells seem to be more sensitive to iron deprivation, targeting on Tf or TfR1 by blocking their binding or interfering with internalization of the holo-Tf/TfR1 complex can cause iron deprivation and thus kill malignant cells.

Many attempts on treatment of malignant diseases by developing anti-human TfR1 antibodies or TfR1-binding peptides to compete with Tf in receptor binding or obstructing internalization were described in literatures in the past thirty years (see TORTORELLA and KARAGIANNIS. J Membr Biol. 247:291-307, 2014; CANDELARIA et al. Front. Immunol. 17 Mar. 2021. doi.org/10.3389/fimmu.2021.607692 for reviews). TROWBRIDGE and LOPEZ (Proc. Natl Acad Sci USA, 79, 1175-1179, 1982; U.S. Pat. No. 4,434,156) report a murine anti-TfR1 antibody, designated 42/6, which blocks the binding of Tf to TfR1 by a non-competitive mechanism and is able to inhibit the growth of a human T leukemic cell line in S phase of the cell cycle in vitro. Although 42/6 was found to be well-tolerated by patients in a Phase Ia clinical trial, because of its murine IgA isotype, it induced human anti-mouse antibody (HSMS) and was quickly cleared by kidney, causing lack of potency (BROOKS et al. Clin Cancer Res. 1:1259-1265, 1995). MOURA et al. (J Exp Med, 194, 417-425, 2001) reported a more potent neutralizing murine anti-TfR1 IgG2b antibody (A24) which inhibits proliferation of T cells by directly competing with Tf on binding to TfR1 with high affinity ($K_D$=2.7 nM), reducing TfR expression and impairing TfR recycling. In contrast to 42/6, which exerts its antiproliferative effects by blocking the cells at the S phase of the cell cycle, A24 acts by inducing the apoptosis of target cells, and blocked the ex vivo proliferation of adult T-cell leukemia/lymphoma (ATLL), acute myeloid leukemia (AML), and mantle cell lymphoma (MCL) cells (Moura et al. Blood. 103:1838-1845, 2004; CALLENS et al. Leukemia. 22:42-48, 2008; LEPELLETIER. Cancer Res. 67:1145-1154, 2007).

To overcome the lack of efficacy and HAMA response in humans, several chimeric, humanized or fully human antibodies were developed in recent years. As examples, a mouse-human IgG3 chimeric antibody, ch128.1, shows in vivo anti-cancer activities in cell line-derived xenograft (CLDX) models of human multiple myeloma (MM) and AIDS-related non-Hodgkin lymphoma (AIDS-NHL) (DANIELS. J Immunother. 34:500-508, 2011; DANIELS-WELLS. J Immunother. 38:307-310, 2015.), and its humanized version, hu128.1 (IgG1), is also potent in AIDS-NHL CLDX models (DANIELS-WELLS. Cancer Res. 80(16 Suppl):5655, 2020.). The anti-cancer activities of ch128.1 and hu128.1 are thought to be dependent on Fc-mediated antibody-dependent cellular cytotoxicity (ADCC), complement-dependent cytotoxicity (CDC), and antibody-dependent cell phagocytosis (ADCP). Three fully human neutralizing antibodies of the IgG1 isotype were described. PPMX-T003 and H7-IgG1 blocked tumor growth and prolong mouse survival in various leukemia or lymphoma models (SHIMOSAKI et al. Biochem Biophys Res Commun. 485: 144-151, 2017; ZHANG et al. Cancer Res. 77(13 Suppl): 5586, 2017;). More strikingly, Anti-TFRC developed by NAGAI et al. (Cancer Med. 3:108-1099, 2014) inhibits the proliferation of oral squamous cell carcinoma (OSCC) cells both in vitro and in vivo (NEIVEYANS et al. MAbs. 11:593-605, 2019.), suggesting that TfR1 might be applied to treatment of solid tumors in addition to hematopoietic malignancies.

Due to the ubiquitous expression profile of TfR1 on dividing cells, anti-TfR1 antibodies might have a universal antiproliferative activity that are not tolerated by cancer patients. Mild to moderate toxicities of anti-TfR1 antibodies to red blood cell (RBC) progenitors and myeloid progenitor cells have been reported with animal models (CANDELARIA et al. Front. Immunol. 17 Mar. 2021). Although many anti-human TfR1 antibodies showed promising preclinical results, besides 42/6, only CX-2029, an anti-TfR1 antibody drug conjugation (ADC), entered clinical stage and shows dose-dependent hematologic toxicities (anemia, neutropenia and leukopenia) that is manageable by RBC transfusion in a phase I clinal trial (JOHNSON et al. Clin Cancer Res. 27:4521-4530, 2021). Therefore, there is a need for anti-TfR1 antibodies that specifically target cancer cells with minimum cross-reaction with normal cells for use in for cancer treatment.

SUMMARY

MAb11-22.1 mAb, a monoclonal antibody (IgG1, kappa) produced by one of the hybridomas obtained from a mouse immunized with multiple live acute myeloid leukemia (AML) cell lines, was identified as a specific mAb against human TfR1 expressed on AML and other cancer cells. The affinity between MAb11-22.1 mAb and TfR1 is very high ($K_D < 1 \times 10^{-12}$M). In vitro assays showed that MAb11-22.1 mAb had a slight inhibitory effect on the proliferation of cancer cells. An antibody-drug conjugate (ADC) form of MAb11-22.1 chimeric Ab conjugated with Mertansine ("DM1"), N2'-deacetyl-N2'-(3-mercapto-1-oxopropyl)-maytansine (MAb11-22.1-S239C-DM1), significantly inhibited the growth of OCI/AML2 xenograft tumor in an in vivo study.

The coding sequence of the variable region of the light chain of MAb11-22.1 mAb is shown as SEQ ID NO: 1 below.

```
                                               (SEQ ID NO: 1)
  1    gacattgtga tgacacagtc tccatcctcc ctgactgtga cagcaggaga    50
 51    gaaggtcact atgagctgca agtccagtca gagtctgtta aatagtggaa   100
101    atcaaaagaa ctacttgacc tggtaccagc agaaaccagg acagcctcct   150
151    aaactgttga tctactgggc atccacttgg aatctaggg tccctgatca   200
201    cttcacaggc agtggatctg gaacagattt cactctcacc atcagcagtg   250
251    tgcaggctga agacctggca gtctattact gtcagaatga ttatagttat   300
301    cctctcacgt tcggtgctgg gaccaagctg gagctgaaac gggctgatgc   350
351    tgca
```

The translated amino acid sequence in the variable region of the light chain was predicted as SEQ ID NO: 2 below and three antigenic determinant regions (CDRs1 to 3, left to right) are highlighted in bold and underlines.

```
                                               (SEQ ID NO: 2)
IVMTQSPSSL TVTAGEKVTM SCKSSQSLLN SGNQKNYLTW
YQQKPGQPPK LLIYWASTWE SRVPDHFTGS GSGTDFTLTI
SSVQAEDLAV YYCQNDYSYP LTFGAGTKLE LKRADAA
```

The coding sequence of the variable region of the heavy chain of MAb11-22.1 mAb is shown as SEQ ID NO: 3 below.

```
                                               (SEQ ID NO: 3)
  1    gaggtccagc tgcagcagtc tggacctgag ctggtgaagc ctggggcttc    50
 51    agtgaggatt tcctgcaaga cttctggcta caccttcaca aactactata   100
101    tacactggat gaagcagagg cctggacagg gacttgagtg gattggatgg   150
151    atttatcctg gagatggtaa ttctcattac aatgagaagt tcaagggcaa   200
201    gaccacactg actgcagaca aatcctccag cacaggctac atattgctca   250
251    gcagcctgac ctctgaagac tctgcagtct atttctgtac aagagattat   300
301    gataactacg ggggatttgc ttactggggc caagggactc tggtcactgt   350
351    ctct
```

The translated amino acid sequence in the variable region of the heavy chain was predicted as SEQ ID NO: 4 below and three antigenic determinant regions (CDRs1 to 3, left to right) are highlighted in bold and underlines.

```
                                               (SEQ ID NO: 4)
EVQLQQSGPE LVKPGASVRI SCKTSGYTFT NYYIHWMKQR
PGQGLEWIGWI YPGDGNSHYN EKFKGKTTLT ADKSSSTGYI
LLSSLTSEDS AVYFCTRDYD NYGGFAYWGQG TLVTVSA
```

This invention relates to Binding Agents (defined below), including antibodies (defined below) such as monoclonal antibodies and fragments and derivatives thereof, which include one or more light chain CDR regions at least 70% (e.g., 70%, 75%, 80%, 85%, 90%, 95%, 97%, 98%, or 99%) identical to the CDR regions of the TfR1-specific mAb, designated MAb11-22.1; including a light chain variable region at least 70% (e.g., 70%, 75%, 80%, 85%, 90%, 95%, 97%, 98%, or 99%) identical to SEQ ID NO: 2. Optionally, the Binding Agent heavy chain variable region is at least 70% (e.g., 70%, 75%, 80%, 85%, 90%, 95%, 97%, 98%, or 99%) identical to SEQ ID NO: 4. The Binding Agent can include a region like the light chain CDR1 of MAb11-22.1, at least 70% (e.g., 70%, 75%, 80%, 85%, 90%, 95%, 97%, 98%, or 99%) identical to the sequence QSLLNSGNQK-NYLT (SEQ ID NO.: 5). The Binding Agent can include a region like the light chain CDR2 of MAb11-22.1, at least 70% (e.g., 70%, 75%, 80%, 85%, 90%, 95%, 97%, 98%, or 99%) identical to the sequence WASTWESR (SEQ ID NO.: 6). The Binding Agent can include a region like the light chain CDR3 of MAb11-22.1, at least 70% (e.g., 70%, 75%, 80%, 85%, 90%, 95%, 97%, 98%, or 99%) identical to the sequence: QNDYSYPLT (SEQ ID NO.: 7). The Binding Agent can include a region like the heavy chain CDR1 of MAb11-22.1, at least 70% (e.g., 70%, 75%, 80%, 85%, 90%, 95%, 97%, 98%, or 99%) identical to the sequence KTSGYTFTNYYIH (SEQ ID NO.: 8). The Binding Agent can include a region like the heavy chain CDR2 of MAb11-22.1, at least 70% (e.g., 70%, 75%, 80%, 85%, 90%, 95%, 97%, 98%, or 99%) identical to the sequence WIYPGDGN-SHYNEKFKG (SEQ ID NO.: 9). The Binding Agent can include a region like the heavy chain CDR3 of MAb11-22.1, at least 70% (e.g., 70%, 75%, 80%, 85%, 90%, 95%, 97%, 98%, or 99%) identical to the sequence: TRDYDNYGGFAY (SEQ ID NO.: 10).

The present application relates to the treatment of multiple cancers, which overexpress TfR1, with MAb11-22.1, and Binding Agents (defined below) related to MAb11-22.1, including Binding Agents derived from or having portions at least 70% (e.g., 70%, 75%, 80%, 85%, 90%, 95%, 97%, 98%, or 99%) identical to one or more of the sequences of the light chain and heavy chain CDRs of MAb11-22.1. MAb11-22.1 binds specifically to human TfR1 protein with high affinity and induces internalization of this protein.

The Binding Agents are preferentially used in treating tumor-related diseases including primary and metastatic cancers, e.g., leukemia, lymphoma, multiple myeloma, breast cancer, gliobastoma, prostate cancer, urothelial bladder cancer, esophageal cancer, colorectal cancer, pancreatic cancer, ovarian cancer, liver cancer, gastric cancers, including squamous cell carcinoma of the stomach, gastric adenocarcinoma, small cell carcinoma of the stomach, gastric squamous cell carcinoma, gastric carcinoid tumors, and stomach and duodenal cancers.

The binding agent conjugates preferably include an anti-tumor agent, for example, a cytotoxin, including maytansine or a derivative thereof, Auristatin or a derivative thereof, epothilone or a derivative thereof, paclitaxel or a derivative thereof, or a vinca alkaloid compound; or further including: Combretastatin A-4 phosphate, Combretastatin A-4 and its derivatives, indole-sulfa compounds, vinca alkaloids compounds such as vinblastine, vincristine, vindesine, vinorelbine, vinflunine, vinglycinate, anhydrovinblastine, dolastatins 10 and analogues, halichondrin B and Eribulin, indole-3-oxalyl amides, substituted indol-3-oxalyl amides, podophyllotoxins, 7-diethylamino-3-(2'-benzoxazolyl)-coumarin (DBC), discodermolide, Laulimalide; DNA topoisomerase inhibitors such as camptothecin and its derivatives, mitoxantron; mitoguazone; nitrogen mustard analogues such as Chlorambucil, Chlomaphazine, cyclophosphamide, Estramustine, ifosfamide, Mustine, Nitromin, Melphalan, Novembichin, Phenamet, Phenesterine, Prednimustine, Trofosfamide, Uramustine; nitrosoureas such as Carmustine, streptozotocin, Fotemustine, Lomustine, Nimustine, Ranimustine; antibiotics such as the enediyne antibiotics, Dynemicin, Esperamicin, Neocarzinostatin, Aclacinomycin, Actinomycin, Anthroamycin, Azaserine, Bleomycins, actinomycin C, Carabicin, Idarubicin, Carzinophilin, Carminomycin, Actinomycin D, Daunorubicin, Doxorubicin, 6-diazo-5-oxo-L-norleucine, Adriamycin, Epirubicin, Esorubicin, Idarubicin, Marcellomycin, Mitomycins, Mycophenolic acid, Nogalamycin, Olivomycin, Peplomycin, Bofeimeisu, Puromycin, Adriamycin-Fe, Rodorubicin, Streptonigrin, Streptozocin, Tubercidin, Ubenimex, Zinostatin, Zorubicin; folic acid analogues such as Denopterin, Methotrexate, Pteropterin, Trimetrexate, Edatrexate; Purine analogues such as Fludarabine, 6-mercaptopurine, Thiamiprine, Thioguanine; pyrimidine analogues such as Ancitabine, Gemcitabine, Enoxaparin, Azacitidine, 6-Azauridine, Carmofur, Cytarabine, dideoxyuridine, deoxy-fluorouridine, Fluoruridine; androgens such as Calusterone, Dromostanolone propionate, Epitiostanol, Mepitiostane, Testolactone; anti-adrenal compounds such as Aminoglutethimide, Mitotane, Trilostane; trichothecenes such as T-2 toxin, verracurin A, Roridin A and Anguidine; aziridines such as Benzodopa, Carboquone, Meturedopa and Uredopa; platinum analogs such as Cisplatin, Carboplatin, Oxaliplatin, Miriplatin, Etoposide; anti-androgens such as Flutamide, Nilutamide, Bicalutamide, Leuprolide and Goserelin; protein kinase and proteasome inhibitors.

The Binding Agent is preferably bonded to the anti-tumor agent using a linker. Bonding can be done as described for linking Mertansine (DM1) below, i.e., using site-specific conjugation to conjugate a thiol group in the Binding Agent to the anti-tumor agent. A number of other bonding methods can be used.

In some embodiments, linkers may be used in the conjugate bonding which can be composed of flexible residues like glycine and serine (one example being four glycine residues followed by a serine, repeated; or simply repeated glycine residues) so that the adjacent protein domains are free to move relative to one another. If one desires to maintain distance between domains, so they cannot interact, rigid linkers are preferred; one example being (repeating): glutamic acid, three alanine residues, lysine. Another rigid linker is (repeating): any amino acid residue and proline. Linkers can be either non-cleavable (e.g., thioether, SMCC, PEG linkers), or cleavable linkers, such as valine-citrulline (Val-Cit, VC) dipeptide, glutamic acid-valine-citrulline (Glu-Val-Cit, GVC) tripeptide and disulfide linkers. U.S. Pat. No. 9,310,373 "Molecular conjugate" discloses a number of hydrazide thiol linkers, and making conjugates with them. U.S. Pat. No. 8,518,891 discloses a linker with an aminoarylmethyl or aminoheteroaryl moiety. Bi-functional linkers have also been described. See U.S. Pat. No. 11,040,084.

The appropriate dosage range and dosing regimens can be extrapolated from the in vivo and in vitro experimental results, set forth herein. The Binding Agents are preferentially delivered in a pharmaceutical formulation for therapy; and they can also be used in diagnosis, purification or screening for selection of other Binding Agents.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A illustrates that MAb11-22.1 mAb interacted with nine human AML cell lines on the cell surfaces, but not with human PBMC in a Fluorescence-activated cell sorting (FACS) assay (left panel). An isotype control Ab was used as a negative control in this assay (right panel). Fluorescein AffiniPure Goat Anti-Mouse IgG, Fcγ fragment specific (anti-Mo IgG Fc-FITC, Jackson ImmunoResearch Laboratories) at 1:800 dilution was used for detection. The assay was performed at 4° C. MFI: mean fluorescence intensity.

FIG. 1B shows the images of immunocytochemistry (ICC) assay of MAb11-22.1 mAb bound to the surfaces of NB4 or THP-1 cells (upper panels), whereas the isotype control Ab did not stain these cells (lower panels). The AML cells were fixed to glass slides by cytospin in 4% paraformaldehyde. After antigen retrieval, the cells were blocked with 1% bovine serum albumin (BSA) in PBST and then incubated with the primary antibodies for one hour, followed by one-hour incubation with 1:1000 diluted Peroxidase AffiniPure Goat Anti-Mouse IgG (subclasses 1+2a+2b+3), Fcγ Fragment Specific (Jackson ImmunoResearch Laboratories). The cells were stained with 3,3'-diaminobenzidine (DAB) and counterstained with hematoxylin.

FIG. 1C is a Western blot showing that MAb11-22.1 mAb hybridized with a protein band present in ALL cell (Raji) and AML cell (NB4, OCI/AML2, and THP-1) whole cell lysates. This targeting protein was approximately 250 kDa under the non-reducing condition (left panel) or 110 kDa under the reduced condition (right panel). Chinese hamster ovary (CHO) cell lysate was used as a negative control. β-actin was simultaneously detected by a specific mouse mAb as a sample loading control. Peroxidase AffiniPure Goat Anti-Mouse IgG Fcγ at 1:10,000 dilution was used for detection.

FIG. 2A is a representative silver-stained SDS-PAGE image of the immunoprecipitation (IP) samples obtained by reaction of MAb11-22.1 mAb with the AML whole cell lysate. The IP samples were reduced and equally loaded onto Lanes 1 and 2, and the target bands of approximately 110 kDa as indicated were excised for LC-MS/MS analysis. Reduced MAb11-22.1 mAb was loaded at 8 ng in Lane 4 as a control. The protein bands were detected with ProteoSilver™ Silver Stain Kit (MilliporeSigma) following manufacturer's protocol. MW: molecular weight marker; HC: heavy chain; LC: light chain.

FIG. 2B depicts a Western blot of the non-reduced ALL and AML whole cell lysate samples simultaneously probed with MAb11-22.1 mAb and anti-β-actin mAb. The left lane was loaded with 1.2 of recombinantly expressed TfR1 extracellular domain (rTfR1-ECD, ACRO Biosciences) as a positive control and the right two lanes were loaded with CHO cell lysate in two concentrations (1× and 2×) as negative controls. Peroxidase AffiniPure Goat Anti-Mouse IgG Fcγ at 1:20,000 dilution was used for detection.

FIG. 2C shows confirmation of direct interaction between MAb11-22.1 mAb and the extracellular domain of TfR1 by ELISA. The plate was coated with 0.1 µg/mL of purified rTfR1-ECD containing a C-terminal 6×His tag. A mouse anti-6×His mAb and an isotype control Ab were used as positive and negative controls, respectively. All the primary antibodies were in 3-fold serial dilutions with a starting concentration of 3 µg/mL. Peroxidase AffiniPure Goat Anti-Mouse IgG Fcγ at 1:6,000 dilution was used for detection.

FIG. 2D shows results from an FACS assay of CHO cells with or without recombinant expression of human TfR1-GFP fusion protein (rTfR1-GFP) on the cell membrane. CHO cells were not reactive with MAb11-22.1 mAb #1 or #2 (two different purification batches), or a commercially available anti-human TfR1 control mAb (R&D systems). However, after reconstituting TfR1 on cell membrane, MAb11-22.1 mAb #1, #2, and anti-TfR1 control mAb could bind to the cell surface. MAb11-22.1 mAb had higher affinity than anti-TfR1 control mAb. The secondary antibody used was R-Phycoerythrin (R-PE) AffiniPure Goat Anti-Mouse IgG (subclasses 1+2a+2b+3), Fcγ Fragment Specific (Jackson ImmunoResearch Laboratories) at 1:800 dilution.

FIGS. 3A to 3C are the data outputs from the ForteBio Octet® QK System showing the affinity and kinetics between MAb11-22.1 mAb and rTfR1-ECD.

FIG. 3A is the aligned sensorgram traces showing association and dissociation curves for MAb11-22.1 mAb binding to 20 nM rTfR1-ECD (left panel) or 300 nM goat anti-mouse (H+L) Fab (positive control, right panel) extracted from raw data by the fortebio software. The ForteBio Octet® QK system was equipped with anti-mouse Fc capture (AMC) biosensors to immobilize 10 nM or 50 nM MAb11-22.1 mAb. Duration of the key steps were as follows: 60 s (s: second or sec), baseline in kinetics buffer, 450 s immobilization of MAb11-22.1 mAb, 120 s baseline/washing in kinetics buffer, 450 s antigen association, followed by 3000 s dissociation in kinetics buffer only. Upper curve: 10 nM mAb; lower curve: 50 nM mAb.

FIG. 3B shows the kinetic data of binding between MAb11-22.1 mAb and rTfR1-ECD, which started at 20 nM and was serially diluted by 2.5 fold. Association occurred quickly and no dissociation was detected within the observation period (3000 seconds).

FIG. 3C shows the kinetic data of binding between MAb11-22.1 mAb and the positive control, goat anti-mouse IgG (H+L) Fab, in serial dilutions to verify the reliability of the equipment.

FIGS. 5A to 5C are FACS results of MAb11-22.1 mAb binding to human PBMC and bone marrow (BM) cells from healthy adults, and to BM cells of AML patients.

FIG. 5A shows that MAb11-22.1 mAb did not bind to either normal human PBMC (Stanford Blood Center) or normal human BM cells (Human Cells, Fremont, CA) regardless of the mAb concentrations. An isotype control Ab served as a negative control. The mAbs were serially diluted eight fold starting at 20 µg/mL, and were detected with 1:800 diluted anti-Mo IgG Fc-FITC.

FIG. 5B shows that MAb11-22.1 mAb bound to BM cells from an AML patient in a dose-dependent manner.

FIG. 5C is the scatter plots of PBMC and BM cells stained by different mAbs. Cutoffs for considering a cell surface marker positive or negative are shown as solid lines and subdivide the graph into four quadrants. FITC-labeled mouse anti-human CD34 mAb (Miltenyi, Cambridge, MA) that was specific for hematopoietic stem cells confirmed the presence of stem cells in the BM sample (lower left panel). MAb11-22.1 mAb and the isotype control Ab stained a small portion of the BM cells as a result of stickiness of BM cells.

FIG. 5D shows that the erythrocytes present in PBMC and BM cell clusters that were stained by anti-human CD233-PE mAb (Miltenyi) were not reactive with MAb11-22.1 mAb or the isotype control Ab.

FIG. 6A compares the fluorescence intensities on cell surface of three leukemia cell lines (OCI/AML2, NB4, and Raji) individually stained with MAb11-22.1 mAb, a mouse anti-human CD20 mAb, or an isotype control Ab at different conditions in a FACS assay. Cells were incubated with each mAb for an hour at 4° C., followed by washing with cold PBS and incubation in culture medium at 4° C. or 37° C. Cell staining was performed with anti-Mo IgG Fc-FITC at 30 minutes, 1 hour, and 2 hours, respectively. At 4° C., MAb11-22.1 mAb bound to the surfaces of the two AML cell lines in a dose-dependent manner, but not to Raji cells, and it was quickly internalized after transferring to 37° C. (left panels). The anti-CD20 mAb that interacted with Raji cells, but not AML cells, could be partially internalized by Raji cells at 37° C. (middle panels). An isotype control Ab that bound to neither cell line was used as a negative control (right panels).

FIG. 6B are representative fluorescent images of MAb11-22.1 mAb binding to and being internalized by the OCI/AML2 cell line. Cells in duplicate 96-well culture plates were incubated with different concentrations of CF488-labeled MAb11-22.1 mAb or CF488-labeled isotype control Ab in DMEM culture medium for one hour at 4° C., and then washed with ice-cold PBS to remove the mAbs. Cells in one plate were resuspended in ice-cold PBS for photographing using Keyence fluorescence microscope with 400× magnification, whereas cells in the duplicated plate were resuspended in warm SFM and incubated at 37° C. for an hour to allow internalization of the mAb. MAb11-22.1 mAb-CF488 bound to the surface of OCI/AML2 cells at 4° C., but was mainly internalized after one-hour incubation at 37° C. As a control, the CF488-labeled isotype control mAb did not stain the cells and was not taken up by the cells (right panels). The pictures were taken with the same settings. Scale bars indicate 100 μm.

FIG. 6C are representative images showing dose-related incrementation of binding and internalization of MAb11-22.1 mAb-CF488 by MDA-MB-231 cells. The assay protocol was the same as that in FIG. 6B except that a higher concentration (5 μg/mL) of mAb was used. At 4° C., MAb11-22.1 mAb-CF488 was not only located on the surface of MDA-MB-231 cells, but also present inside the cells, indicating high tendency of MAb11-22.1 mAb-CF488 internalization by MDA-MB-231 cell line. After one-hour incubation at 37° C., the majority of MAb11-22.1 mAb-CF488 was internalized. The CF488-labeled isotype control mAb-CF488 did not stain the cells or being uptaken by the cells (right panels). The pictures were taken at 400× magnification with the same exposure time. Scale bars indicate 100 μm.

FIG. 8A shows the fitting view of the association and dissociation curves and the data table of the binding kinetics between MAb11-22.1 cAb and rTfR1-ECD at 2.5-fold serial dilutions (50, 20, 8. 3.2, and 1.28 nM). The Octet QK system was equipped with anti-human Fc capture (AHC) biosensors to immobilize 50 nM or 10 nM MAb11-22.1 cAb. Duration of the key steps were as follows: 60-s baseline in kinetics buffer, 450-s immobilization of MAb11-22.1 cAb, 120-s baseline/washing in kinetics buffer, 450-s antigen association with immobilized MAb11-22.1 cAb, followed by 3600-s dissociation in kinetics buffer only. No decay in the binding signal was detected during the time allowed for dissociation, so the $K_D$ of MAb11-22.1 cAb and rTfR1-ECD was <1 pM.

FIG. 8B is the fitting view of the kinetic analysis of the positive control, goat anti-human (H+L) Fab, with 3-fold serial dilutions (300, 100, 33.3, 11.1, and 3.7 nM) in binding to 50 nM MAb11-22.1 cAb. The calculated $K_D$ was 2.18 nM.

DETAILED DESCRIPTION

Figure 1A:
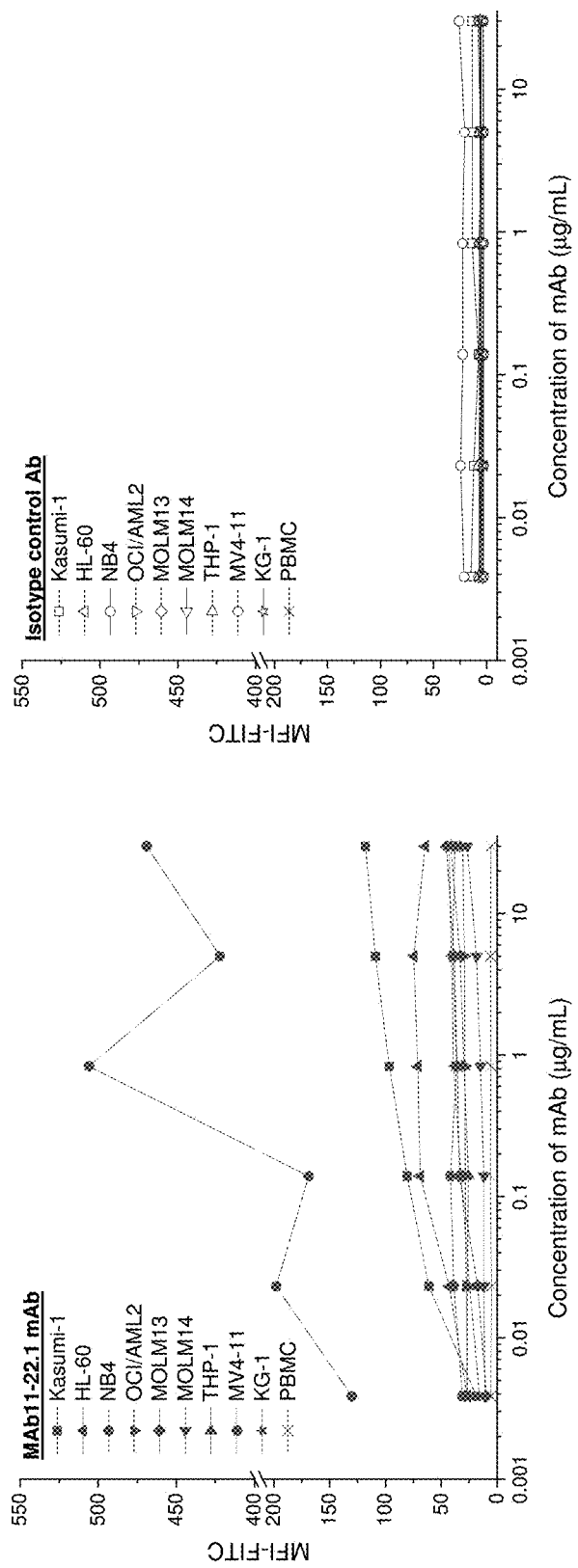
FIGS. 1A to 1C show that MAb11-22.1 mAb bound directly with AML cell lines, but not to healthy human peripheral blood mononuclear cell (PBMC).

It should be understood that unless the context clearly dictates otherwise, the singular forms "a", "an" and "the" include plural forms. Monoclonal antibodies are referred to sometimes as "mAbs." The terms "Binding Agent" and "antibody," singular and plural forms, are used interchangeably.

The Binding Agents of the invention include MAb11-22.1-like or MAb11-22.1-derived antibodies, antibody fragments, fusion proteins, or, an antibody-derived or modified chimeric antibody receptor (CAR), including single-chain variable fragments (scFv) fused to intracellular signaling domains, e.g., the zeta chain of CD3 (CD3ζ). CAR is preferably expressed in CAR immune effector cells including but not limited to T cells, NK cells and macrophages.

The term Binding Agent(s) includes an antibody (both are interchangeably used in plural form) which is an immunoglobulin molecule capable of binding to a target antigen, such as an antigen on gastric cancer cells, through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')$_2$, Fv, Fd, rIgG, single chain (scFv) or sc(Fv)$_2$, mutants thereof, fusion proteins comprising an antibody portion, humanized antibodies, chimeric antibodies, diabodies, multispecific antibodies (e.g., bispecific antibodies), single domain antigen binding (SDAB) molecules, a VH or VL domain, or a VHH domain, and any other modified configuration of the immunoglobulin molecule that comprises an antigen recognition site of the required specificity, including glycosylation variants of antibodies, amino acid sequence variants of antibodies, and covalently modified antibodies. Also included are antibody-drug conjugates.

An antibody includes antibodies of any class, such as IgD, IgE, IgG, IgA, or IgM (or a sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2.

Antibodies described herein can be murine, rat, human, or any other origin (including chimeric or humanized antibodies, including as described in U.S. Pat. No. 7,317,091B2, and including such antibodies generated by affinity maturation). In some examples, the antibody comprises a modified constant region, such as a constant region that is immunologically inert, e.g., does not trigger complement mediated lysis, or does not stimulate antibody-dependent cell mediated cytotoxicity (ADCC). ADCC activity can be assessed using methods disclosed in U.S. Pat. No. 5,500,362.

Humanized antibodies refer to forms of non-human (e.g. murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody. Humanized antibodies may also involve affinity maturation. See Jones et al., Nature, 321:522-525 (1986); Riechmann et al., Nature, 332:323-327 (1988); Verhoeyen et al., Science, 239: 1534-1536 (1988).

In another example, the antibody described herein is a chimeric antibody, which can include a heavy constant region and a light constant region from a human antibody. See, e.g., Morrison et al. (1984) Proc. Natl. Acad. Sci. USA 81, 6851; Neuberger et al. (1984) Nature 312, 604; and Takeda et al. (1984) Nature 314:452. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region. See U.S. Pat. No. 4,816,567.

The "percent identity" of two amino acid sequences can be determined arithmetically, by counting and comparing, for the shorter sequences described or claimed herein, or by using the algorithm of Karlin and Altschul Proc. Natl. Acad. Set USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al, Nucleic Acids Res. 25(17):3389-3402, 1997. When utilizing BLAST and Gapped BLAST programs, the default parameters of the respective programs (e.g., XBLAST and NBLAST) can be used.

Making Binding Agents

A number of methodologies have been developed to prepare chimeric, humanized or human antibodies for human in vivo therapeutic applications. The most used methodology is to prepare mouse mAbs using hybridoma methodology and then to humanize the mAbs by converting the framework regions of the VH and VL domains and constant domains of the mAbs into homologous human framework regions of human VH and VL domains and constant regions of a desirable human γ immunoglobulin isotype and subclass. See U.S. Pat. No. 5,225,539.

Monoclonal antibodies can be made by the conventional hybridoma technology. Kohler et al., Nature, 256:495 (1975). In the hybridoma method, a mouse or other appropriate host animal, such as a hamster or rabbit, is immunized as hereinabove described to elicit lymphocytes that produce or are capable of producing antibodies that will specifically bind to the protein used for immunization. Alternatively, lymphocytes may be immunized in vitro.

To prepare monoclonal antibodies, immune cells are collected from the mammal immunized with the antigen and checked for the increased level of desired antibodies in the serum as described above, and are subjected to cell fusion. The immune cells used for cell fusion are preferably obtained from spleen. Other preferred parental cells to be fused with the above immunocyte include, for example, myeloma cells of mammalians, and more preferably myeloma cells having an acquired property for the selection of fused cells by drugs.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)).

The above immunocyte and myeloma cells can be fused according to known methods, for example, the method of Milstein et al. (Galfre et al., Methods Enzymol. 73:3-46, 1981). Lymphocytes are fused with myeloma cells using a suitable fusing agent, such as polyethylene glycol, to form a hybridoma cell (Goding, Monoclonal Antibodies: Principles and Practice, pp. 59-103 (Academic Press, 1986)). Resulting hybridomas obtained by the cell fusion may be selected by cultivating them in a standard selection medium, such as HAT medium (hypoxanthine, aminopterin, and thymidine containing medium). The cell culture is typically continued in the HAT medium for several days to several weeks, the time being sufficient to allow all the other cells, with the exception of the desired hybridoma (non-fused cells), to die. Then, the standard limiting dilution is performed to screen and clone a hybridoma cell producing the desired antibody.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay. Measurement of absorbance in enzyme-linked immunosorbent assay (ELISA), enzyme immunoassay (EIA), radioimmunoassay (RIA), and/or immunofluorescence may be used to measure the antigen binding activity of the antibody.

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography. In addition, the hybridoma cells may be grown in vivo as ascites tumors in an animal; e.g., in the abdominal cavity of a mouse.

The obtained monoclonal antibodies can be purified by, for example, ammonium sulfate precipitation, a protein A or protein G column, DEAE ion exchange chromatography, or an affinity column to which the protein of the present invention is coupled.

The monoclonal antibodies thus obtained can be also recombinantly prepared using genetic engineering techniques (see, for example, Borrebaeck C. A. K. and Larrick J. W. Therapeutic Monoclonal Antibodies, published in the United Kingdom by MacMillan Publishers LTD, 1990). A DNA encoding an antibody may be cloned from an immune cell, such as a hybridoma or an immunized lymphocyte producing the antibody, inserted into an appropriate vector, and introduced into host cells to prepare a recombinant antibody. Recombinant techniques are described in the literature, particularly in Sambrook et al., MOLECULAR CLONING: A LABORATORY MANUAL, Second edition, Cold Spring Harbor Laboratory Press, 1989, and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; and Kontermann and Dübel, ANTIBODY ENGINEERING, Springer Lab manual, Springer-Verlag Berlin Heidelberg, 2001) and the like.

When the obtained antibody is to be administered to humans in treatment, a human antibody or a humanized antibody is preferable for reducing immunogenicity. For example, transgenic animals having a repertory of human antibody genes may be immunized with the whole cell or an antigen(s) selected from human cell proteins, or their lysates. Antibody producing cells are then collected from the animals and fused with myeloma cells to obtain hybridomas, from which human antibodies against the antigen can be prepared. Alternatively, an immune cell, such as an immunized lymphocyte, producing antibodies may be immortalized by an oncogene and used for preparing monoclonal antibodies.

DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells serve as a preferred source of such cDNA. Once isolated, the DNA may be placed into expression vectors, which are then transfected into host cells such as E. coli cells, simian COS cells, Chinese hamster ovary (CHO) cells, or myeloma cells that do not otherwise produce immunoglobulin protein, to produce monoclonal antibodies in the recombinant host cells. Review articles on recombinant expression in bacteria of DNA encoding the antibody include Skerra et al., Curr. Opinion in Immunol., 5:256-262 (1993) and Pluckthun, Immunol. Rev., 130: 151-188 (1992).

DNAs encoding the antibodies produced by the hybridoma cells described above can be genetically modified, via routine technology, to produce genetically engineered antibodies. Genetically engineered antibodies, such as humanized antibodies, chimeric antibodies, single-chain antibodies, diabodies, bi-specific antibodies and multi-specific antibodies, can be produced via, e.g., conventional recombinant technology. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, including chimeric or humanized antibodies can be prepared that have the binding specificity of a target antigen.

Alternatively, certain transgenic animals (e.g., mice) are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germline immunoglobulin gene array in such germline mutant mice will result in the production of human antibodies upon antigen challenge.

See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993). See also the Xenomouse from Amgen, Inc. (Fremont, Calif.) and HuMAb-MouseR™ and TC Mouse™ from Medarex, Inc. (Princeton, N.J.). In another alternative, antibodies may be made recombinantly by phage display technology. See, for example, U.S. Pat. Nos. 5,565,332; 5,580,717; 5,733, 743; and 6,265,150; and Winter et al., (1994) Annu. Rev. Immunol. 12:433-455; (Hoogenboom et al., J. Mol. Biol., 227:381 (1991); Marks et al., J. Mol. Biol., 222:581-597 (1991). Alternatively, the phage display technology (McCafferty et al., (1990) Nature 348:552-553) can be used to produce human antibodies and antibody fragments in vitro, from immunoglobulin variable (V) domain gene repertoires from unimmunized donors.

F(ab')$_2$ fragments can be produced by pepsin digestion or other proteolytic digestion of intact antibodies (see, e.g., Morimoto et al., Journal of Biochemical and Biophysical Methods 24: 107-117 (1992) and Brennan et al., Science 229: 81 (1985)). Fab fragments that can be generated by reducing the disulfide bridges of F(ab')$_2$ fragments. Such fragments can now also be produced directly by recombinant host cells. For example, the antibody fragments can be isolated from an antibody phage library. Alternatively, F(ab') 2-SH fragments can be directly recovered from *E. coli* and chemically coupled to form F(ab')$_2$ fragments (Carter et al., Bio/Technology 10: 163-167 (1992)). According to another approach, F(ab')$_2$ fragments can be isolated directly from recombinant host cell culture.

U.S. Pat. No. 5,932,448, discloses making of bispecific antibodies with Fab' portions joined by a leucine zipper; U.S. Pat. No. 7,538,196, discloses making of bispecific antibodies where portions are joined with a linker; U.S. Pat. No. 8,148,496 discloses a multi-specific Fv antibody construct having at least four variable domains which are linked with each other via peptide linkers.

US Publ'n No. 20170335281 describes making of a genetically modified T cell expressing a CAR that comprises an antigen binding domain that binds to a cancer associated antigen. The same general techniques can be applied to modify T cells or other immune effector cells to express one or more of CDR1, CDR2 and CDR3 of MAb11-22.1, as the antigen binding domain, for cancer treatment. The antigen binding domain of the CAR polypeptide molecule can include any antibody, antibody fragment, an scFv, a Fv, a Fab, a, F(ab')$_2$ a single domain antibody (SDAB), a VH or VL domain, or a VHH domain.

Single domain antibody (sdAb) molecules are disclosed in WO 9404678 and Hamers-Casterman, C. et al. (1993) Nature 363:446-448. The sdAb molecule is a naturally occurring single domain antigen binding molecule known as heavy chain devoid of light chains. In one type of sdAb, the variable domain is derived from a heavy chain molecule naturally devoid of light chain that can be derived from Camelidae species, for example in camel, llama, dromedary, alpaca and guanaco. Other species besides Camelidae may also produce heavy chain molecules naturally devoid of light chain. The sdAb molecules can be recombinant, CDR-grafted, humanized, camelized, de-immunized and/or in vitro generated (e.g., selected by phage display).

Any of the Binding Agents above can be used in an antibody-drug conjugate (ADC), which targets to cancer cells, by linking it to a cytotoxin for the cancerous cells. See U.S. Pat. No. 9,764,041; US Publ'n No. 20170151343.

High Affinity Antibody Variants

Antibodies with variations of the sequences set forth herein are within the scope of the invention. One type of variant is a high affinity variant, as set forth below.

Antibodies should be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved.

Examples of framework region residues to modify include those which non-covalently bind target directly (Amit et al. Science 233: 747-753 (1986)); interact with/effect the conformation of CDR (Chothia et al. J. Mol. Biol. 196: 901-917 (1987)); and/or participate in the VL-VH interface (EP 239 400 B1). In certain embodiments, modification of one or more of such framework region residues results in an enhancement of the binding affinity of the antibody for the target of interest.

Nucleic acid molecules encoding amino acid sequence variants are prepared by a variety of methods known in the art. These methods include, but are not limited to, oligonucleotide-mediated (or site-directed) mutagenesis, polymerase chain reaction (PCR) mutagenesis, and cassette mutagenesis of an earlier prepared variant or a non-variant version of the species-dependent antibody. The preferred method for generating variants is an oligonucleotide-mediated synthesis. In certain embodiments, the antibody variant will only have a single hypervariable region residue substituted, e.g. from about two to about fifteen hypervariable region substitutions.

One method for generating the library of variants is by oligonucleotide mediated synthesis. Three oligonucleotides of approximately 100 nucleotides each may be synthesized spanning the entire light chain or heavy chain variable region. Each oligonucleotide may comprise: (1) a 60 amino acid stretch generated by the triplet (NNK).sub.20 where N is any nucleotide and K is G or T, and (2) an approximately 15-30 nucleotide overlap with either the next oligo or with the vector sequence at each end. Upon annealing of these three oligonucleotides in a PCR reaction, the polymerase will fill in the opposite strand generating a complete double stranded heavy chain or light chain variable region sequence. The number of triplets may be adjusted to any length of repeats and their position within the oligonucleotide may be chosen so as to only substitute amino acids in a given CDR or framework region. By using (NNK), all twenty amino acids are possible at each position in the encoded variants. The overlapping sequence of 5-10 amino acids (15-30 nucleotides) will not be substituted, but this may be chosen to fall within the stacking regions of the framework, or may substituted by a separate or subsequent round of synthesis. Methods for synthesizing oligonucleotides are well known in the art and are also commercially available. Methods for generating the antibody variants from these oligonucleotides are also well known in the art, e.g., PCR.

The library of heavy and light chain variants, differing at random positions in their sequence, can be constructed in any expression vector, such as a bacteriophage, each of which contains DNA encoding a particular heavy and light chain variant.

Following production of the antibody variants, the biological activity of variant relative to the parent antibody is determined. As noted above, this involves determining the binding affinity of the variant for the target. Numerous high-throughput methods exist for rapidly screen antibody variants for their ability to bind the target of interest.

One or more of the antibody variants selected from this initial screen may then be screened for enhanced binding affinity relative to the parent antibody. One common method for determining binding affinity is by assessing the association and dissociation rate constants using a BIAcore surface plasmon resonance system (BIAcore, Inc.). A biosensor chip is activated for covalent coupling of the target according to the manufacturer's (BIAcore) instructions. The target is then diluted and injected over the chip to obtain a signal in response units (RU) of immobilized material. Since the signal in RU is proportional to the mass of immobilized material, this represents a range of immobilized target densities on the matrix. Dissociation data are fit to a one-site model to obtain $K_{off}\pm$S.D. (standard deviation of measurements). Pseudo-first order rate constant (Ks) are calculated for each association curve, and plotted as a function of protein concentration to obtain $K_{on}\pm$S.D. (standard error of fit). Equilibrium dissociation constants for binding, $K_d$'s, are calculated from SPR measurements as $K_{off}/K_{on}$. Since the equilibrium dissociation constant, $K_D$, is inversely proportional to $K_{off}$, an estimate of affinity improvement can be made assuming the association rate ($K_{on}$) is a constant for all variants.

The resulting candidate(s) with high affinity may optionally be subjected to one or more further biological activity assays to confirm that the antibody variant(s) with enhanced binding affinity still retain the desired therapeutic attributes, as can be tested in the assays described in the examples below. The optimal antibody variant retains the ability to bind the target with a binding affinity significantly higher than the parent antibody.

The antibody variant(s) so selected may be subjected to further modifications oftentimes depending upon the intended use of the antibody. Such modifications may involve further alteration of the amino acid sequence, fusion to heterologous polypeptide(s) and/or covalent modifications such as those elaborated below. For example, any cysteine residues not involved in maintaining the proper conformation of the antibody variant may be substituted, generally with serine, to improve the oxidative stability of the molecule and prevent aberrant crosslinking. Conversely, (a) cysteine bond(s) may be added to the antibody to improve its stability (particularly where the antibody is an antibody fragment such as an Fv fragment).

Formulations

After preparation of a suitable antibody, it can be prepared in a formulation for administration to a subject. A lyophilized formulation is preferred, which as a first step, requires preparing a pre-lyophilized formulation. The amount of antibody in the pre-lyophilized formulation is determined taking into account the desired dose volumes, mode(s) of administration, etc. The protein is generally present in solution. For example, the protein may be present in a pH-buffered solution at a pH from about 4-8, and preferably from about 5-7. Exemplary buffers include histidine, phosphate, Tris, citrate, succinate and other organic acids. The buffer concentration can be from about 1 mM to about 20 mM, or from about 3 mM to about 15 mM, depending, for example, on the buffer and the desired isotonicity of the formulation (e.g. of the reconstituted formulation). The preferred buffer is histidine as it can have lyoprotective properties. Succinate is also a useful buffer.

The lyoprotectant is added to the pre-lyophilized formulation. In preferred embodiments, the lyoprotectant is a non-reducing sugar such as sucrose or trehalose. The amount of lyoprotectant in the pre-lyophilized formulation is generally such that, upon reconstitution, the resulting formulation will be isotonic, as preferred, though hypertonic reconstituted formulations may also be suitable. In addition, the amount of lyoprotectant must not be too low such that an unacceptable amount of degradation/aggregation of the protein occurs upon lyophilization.

Where the lyoprotectant is a sugar (such as sucrose or trehalose) and the protein is an antibody, exemplary lyoprotectant concentrations in the pre-lyophilized formulation are from about 10 mM to about 400 mM, and preferably from about 30 mM to 5 about 300 mM, and most preferably from about 50 mM to about 100 mM.

The ratio of protein to lyoprotectant is selected for each protein and lyoprotectant combination. In the case of an antibody as the protein of choice and a sugar (e.g., sucrose or trehalose) as the lyoprotectant for generating an isotonic reconstituted formulation with a high protein concentration, the molar ratio of lyoprotectant to antibody may be from about 100 to about 1500 moles lyoprotectant to 1 mole antibody, and preferably from about 200 to about 1000 moles of lyoprotectant to 1 mole antibody, including from about 200 to about 600 moles of lyoprotectant to 1 mole antibody.

In preferred embodiments, it has been found to be desirable to add a surfactant to the pre-lyophilized formulation. Alternatively, or in addition, the surfactant may be added to the lyophilized formulation and/or the reconstituted formulation. Exemplary surfactants include nonionic surfactants such as polysorbates (e.g. polysorbates 20 or 80); poloxamers (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palnidopropyl-, or isostearamidopropyl-betaine (e.g lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.), polyethyl glycol, polypropyl glycol, and copolymers of ethylene and propylene glycol (e.g. Pluronics, PF68 etc). The amount of surfactant added is such that it reduces aggregation of the reconstituted protein and minimizes the formation of particulates after reconstitution. For example, the surfactant may be present in the pre-lyophilized formulation in an amount from about 0.001-0.5%, and preferably from about 0.005-0.05%.

A mixture of the lyoprotectant (such as sucrose or trehalose) and a bulking agent (e.g. mannitol or glycine) may be used in the preparation of the pre-lyophilization formulation. The bulking agent may allow for the production of a uniform lyophilized cake without excessive pockets therein.

Other pharmaceutically acceptable carriers, excipients or stabilizers such as those described in Remington's Pharmaceutical Sciences 16th edition, Osol, A. Ed. (1980) may be included in the pre-lyophilized formulation (and/or the lyophilized formulation and/or the reconstituted formulation) provided that they do not adversely affect the desired characteristics of the formulation. Acceptable carriers, excipients or stabilizers are nontoxic to recipients at the dosages and concentrations employed and include; additional buffering agents; preservatives; co-solvents; antioxidants including ascorbic acid and methionine; chelating agents such as EDTA; metal complexes (e.g. Zn-protein complexes); biodegradable polymers such as polyesters; and/or salt-forming counterions such as sodium.

The pharmaceutical compositions and formulations described herein are preferably stable, so as to retain its physical and chemical stability and integrity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). Stability can be measured at a selected temperature for a selected time period.

The formulations to be used for in vivo administration must be sterile. This is readily accomplished by filtration through sterile filtration membranes, prior to, or following, lyophilization and reconstitution. Alternatively, sterility of the entire mixture may be accomplished by autoclaving the ingredients, except for protein, at about 120° C. for about 30 minutes.

After the protein, lyoprotectant and other optional components are mixed together, the formulation is lyophilized. Many different freeze-dryers are available for this purpose such as Hu1150® (Hull, USA) or GT20® (Leybold-Heraeus, Germany) freeze-dryers. Freeze-drying is accomplished by freezing the formulation and subsequently subliming ice from the frozen content at a temperature suitable for primary drying. Under this condition, the product temperature is below the eutectic point or the collapse temperature of the formulation.

Typically, the shelf temperature for the primary drying will range from about −30 to 25° C. (provided the product remains frozen during primary drying) at a suitable pressure, ranging typically from about 50 to 250 mTorr. The formulation, size and type of the container holding the sample (e.g., glass vial) and the volume of liquid will mainly dictate the time required for drying, which can range from a few hours to several days (e.g. 40-60 hours). A secondary drying stage may be carried out at about 0-40° C., depending primarily on the type and size of container and the type of protein employed. For example, the shelf temperature throughout the entire water removal phase of lyophilization may be from about 15-30° C. (e.g., about 20° C.). The time and pressure required for secondary drying will be that which produces a suitable lyophilized cake, dependent, e.g., on the temperature and other parameters. The secondary drying time is dictated by the desired residual moisture level in the product and typically takes at least about 5 hours (e.g. 10-15 hours). The pressure may be the same as that employed during the primary drying step. Freeze-drying conditions can be varied depending on the formulation and vial size.

In some instances, it may be desirable to lyophilize the protein formulation in the container in which reconstitution of the protein is to be carried out in order to avoid a transfer step. The container in this instance may, for example, be a 3, 5, 10, 20, 50 or 100 cc vial. As a general proposition, lyophilization will result in a lyophilized formulation in which the moisture content thereof is less than about 5%, and preferably less than about 3%.

At the desired stage, typically when it is time to administer the protein to the patient, the lyophilized formulation may be reconstituted with a diluent such that the protein concentration in the reconstituted formulation is preferably similar to that of the pre-lyophilized formulation.

Reconstitution generally takes place at a temperature of about 25° C. to ensure complete hydration, although other temperatures may be employed as desired. The time required for reconstitution will depend, e.g., on the type of diluent, amount of excipient(s) and protein. Exemplary diluents include sterile water, bacteriostatic water for injection (BWFI), a pH buffered solution (e.g. phosphate-buffered saline), sterile saline solution, Ringer's solution or dextrose solution. The diluent optionally contains a preservative. Exemplary preservatives have been described above, with aromatic alcohols such as benzyl or phenol alcohol being the preferred preservatives. The amount of preservative employed is determined by assessing different preservative concentrations for compatibility with the protein and preservative efficacy testing. For example, if the preservative is an aromatic alcohol (such as benzyl alcohol), it can be present in an amount from about 0.1-2.0% and preferably from about 0.5-1.5%, but most preferably about 1.0-1.2%.

Alternatively, a non-lyophilized formulation may be used, including a Binding Agent and any of the well-known carriers, excipients, buffers, stabilizers, preservatives, adjuvants and other additives described herein and well known in the art.

Dosages and Administration

The formulation described above can be administered to a subject (e.g., a human) in need of the treatment via a suitable route, such as administration by intravenous, intramuscular, intraperitoneal, intracerebrospinal, subcutaneous, intracutaneous, intraarticular, intrasynovial, intrathecal, intradermal, intratumoral, intranodal, intramedulla, oral, inhalation or topical routes; or it may be administered orally, by inhalation spray, topically, rectally, nasally, buccally, vaginally or via an implanted reservoir; and in any case, as a bolus or by continuous infusion over a period of time; or via injectable depot routes of administration such as using 1-, 3-, or 6-month depot injectable or biodegradable materials and methods.

Commercially available nebulizers for liquid formulations, including jet nebulizers and ultrasonic nebulizers are useful for administration. Liquid formulations can be directly nebulized and lyophilized powder can be nebulized after reconstitution. Alternatively, antibodies can be aerosolized using a fluorocarbon formulation and a metered dose inhaler, or inhaled as a lyophilized and milled powder. Where CAR is deployed in the invention, compositions of immune effector cells (e.g., T cells, NK cells) may be injected directly into a tumor, lymph node, or site of infection, or elsewhere.

The subject to be treated by the methods described herein can be a mammal, more preferably a human. Mammals include, but are not limited to, farm animals, sport animals, pets, primates, horses, dogs, cats, mice and rats.

An "effective amount" refers to the amount of active agent required to confer therapeutic effect on the subject, either alone or in combination with one or more other active agents. Effective amounts vary, depending on the particular condition being treated, the severity of the condition, the individual patient parameters including age, physical condition, size, gender and weight, the duration of the treatment, the nature of concurrent therapy (if any), the specific route of administration and like factors, all of which are well known to those of ordinary skill in the art and can be addressed with no more than routine experimentation. It is generally preferred that a maximum dose of the individual components or combinations thereof be used, that is, the highest safe dose according to sound medical judgment. A lower dose or tolerable dose for medical reasons, psychological reasons or other reasons, is also appropriate.

Empirical considerations, such as the antibody half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of the gastric cancer. Alternatively, sustained continuous release formulations of antibody may be appropriate. Various formulations and devices for achieving sustained release are known in the art.

In one example, dosages for an antibody as described herein may be determined empirically in individuals who have been given one or more administration(s) of the antibody. Individuals are given incremental dosages of the antibody. To assess efficacy of the antibody, an indicator of the disease (e.g., tumor growth) can be followed according to routine practice.

Generally, for administration of any of the antibodies described herein, an initial candidate dosage can be extrapolated from the experiments described below. For repeated administrations over several days or longer, depending on the condition, the treatment is sustained until a desired suppression of symptoms occurs or until sufficient therapeutic levels are achieved to alleviate the cancer. An exemplary dosing regimen comprises administering an initial higher dose, followed by a lower maintenance dose. However, other dosage regimens may be useful, depending on the pattern of pharmacokinetic decay that the practitioner wishes to achieve. For example, dosing from one-four times a week is contemplated. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

Conventional methods, known to those of ordinary skill in the art of medicine, can be used to administer the pharmaceutical composition to the subject, depending upon the treatment goal and the cancer site.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like).

For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients.

Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In one embodiment, an antibody is administered via site-specific or targeted local delivery techniques. Examples of site-specific or targeted local delivery techniques include various implantable depot sources of the antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., WO 00/53211 and U.S. Pat. No. 5,981,568, In another embodiment of the present disclosure, an article of manufacture is provided which contains any of the pharmaceutical compositions and formulations described herein (e.g., comprising an antibody or Binding Agent) and provides instructions for its use and/or reconstitution. The article of manufacture comprises a container. Suitable containers include, for example, bottles, vials (e.g., dual chamber vials), syringes (such as dual chamber syringes) and test tubes. The container may be formed from a variety of materials such as glass or plastic. The container holds the formulation and the label on, or associated with, the container may indicate directions for reconstitution and/or use. For example, the label may indicate that the formulation is reconstituted to particular protein concentrations. The container holding the formulation may be a multi-use vial, which allows for repeat administrations (e.g., from 2-6 administrations) of the reconstituted formulation. The article of manufacture may further comprise a second container comprising a suitable diluent (e.g., BWFI). Upon mixing of the diluent and the lyophilized formulation, the final protein concentration in the reconstituted formulation will generally be at least 50 mg/mL. The article of manufacture may further include other materials desirable from a commercial and user standpoint, including other buffers, diluents, filters, needles, syringes, and package inserts with instructions for use.

EXAMPLES

The following Examples are not limiting but only exemplary. Unless otherwise specified, all the cell lines were purchased from American Type Culture Collection (ATCC, Manassas, Va.) and all the secondary antibodies for detection were purchased from Jackson ImmunoResearch Laboratories (West Grove, Pa.). Standard methods were used to manipulate DNA and RNA described in Sambrook et al., Molecular cloning: A laboratory manual; Cold Spring Harbor Laboratory Press, Cold Spring Harbor, N.Y., 1989. All commercial reagents and kits were used according to the manufacturer's instructions unless otherwise stated.

To explore target-specific antibodies for the treatment of cancer, we used a live-cell immunization (LCI) and live-cell high-throughput screening (HTS) technology to generate antibodies specifically targeting human tumor surface antigens, followed by identification of the targets using a combination of proteomic and molecular biological approaches.

Example 1

Generation and Characterization of MAb11-22.1 mAb Specifically Targeting on AML Cell Lines To obtain mAbs against the conformational epitopes on cell surface antigens, a mixture of two human AML cell lines, MV4-11 and THP-1, in Phosphate-buffered saline (PBS) was used for LCI and LC-HTS as described previously (see: WO2014146487A1, WO2017114204, US20210139602A1; Li et al., PLoS One. 2013, 8:e77398). Hybridoma culture supernatants were screened for interaction with a mixture of these two live AML cell lines and counter-screened with human peripheral blood mononuclear cells (PBMC) donated by healthy adults (Stanford Blood Center, Palo Alto, Calif.) in a Fluorescence-activated cell sorting (FACS) assay using BD FACSCalibur™ Flow Cytometer with High Throughput Sampler (HTS) and the data were analyzed with the FlowJo™ software (Becton Dickinson, San Jose, Calif.). Hybridoma colonies that showed strong and specific binding activities to human AML cell lines, but not to human PBMC, were selected for expansion, weaning from conditioned medium, and subcloning following standard protocols (Kohler & Milstein, Nature 1975, 256:495-497; Winter & Milstein, Nature 1991, 349: 293-299). Monoclonal antibodies (mAbs) produced by these colonies were purified with MabSelect™ SuRe™ LX Protein A resin (GE Healthcare, Marlborough, Mass.) for further characterizations.

One mAb, designated as MAb11-22.1 mAb, showed high binding capacities to nearly all nine human AML cell lines tested, but not to human PBMC (FIG. 1A, left panel). Binding signal to NB4 cells, an M3 subtype of AML cell line, was particularly high, followed by Kasumi-1 and HL-60 cell lines. Human TruStain FcX™ Fc Receptor Blocking Solution (Biolegend, San Diego, Calif.) was employed in FACS assays to ensure that the binding was not mediated by interaction between the mAbs and the Fc receptors (FcRs) on AML cell surfaces. Since the isotypes of MAb11-22.1 mAb were IgG1/kappa as determined by IsoStrip™ Mouse Monoclonal Antibody Isotyping Kit (Roche Molecular Systems, Pleasanton, Calif.), an irrelevant mouse antibody of IgG1a/kappa that did not interact with the AML cell lines was used as a negative control (isotype control Ab, FIG. 1A, right panel) to confirm that the interaction between MAb11-22.1 mAb and the AML cell surfaces were mediated specifically by the variable regions of MAb11-22.1 mAb.

Figure 1B:
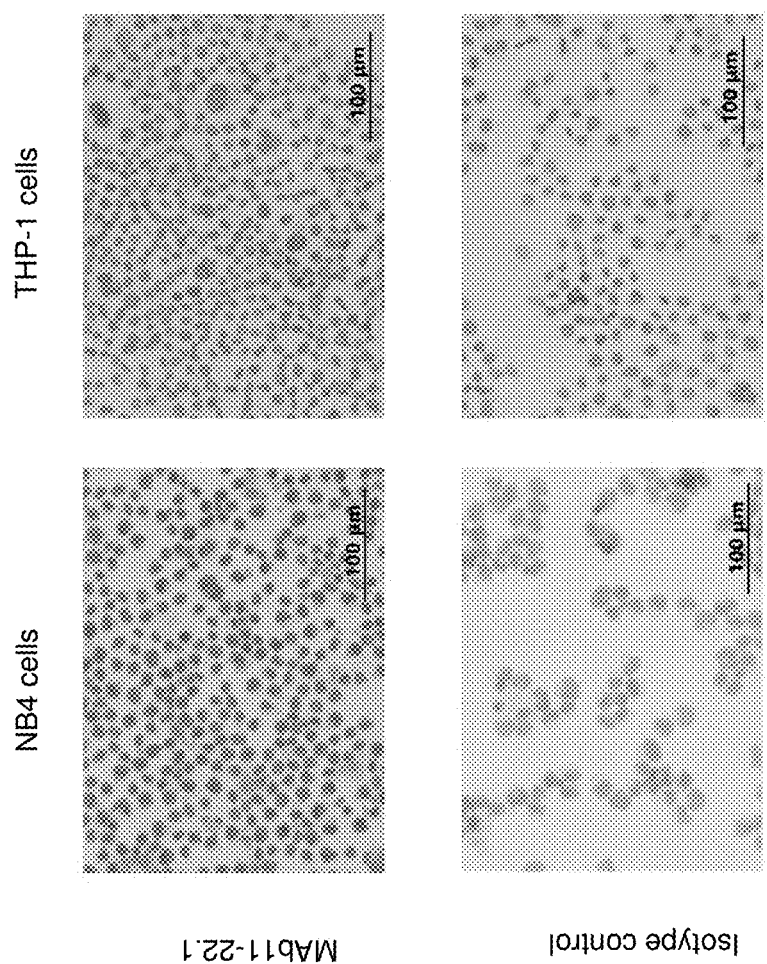

To visualize the binding of MAb11-22.1 mAb to the surface of AML cells, immunocytochemistry (ICC)-based cell surface antibody binding assays were performed. The cultured AML cells were fixed to glass slides by Cytospin 4 (Thermo Fisher Scientific, Waltham, Mass.) in 4% paraformaldehyde. After antigen retrieval by heat, the cells were blocked with goat serum (MilliporeSigma, St. Louis, Mo.) and then incubated with MAb11-22.1 mAb or the isotype control Ab for one hour, followed by one-hour incubation with 1:1000 diluted Peroxidase AffiniPure Goat Anti-Mouse IgG (subclasses 1+2a+2b+3), Fcγ Fragment Specific (anti-Mo IgG Fc-HRP pAb, Jackson ImmunoResearch Laboratories). The cells were stained with 3,3'-diaminobenzidine (DAB) and counterstained with hematoxylin. As shown in FIG. 1B, ICC assays verified that the target for MAb11-22.1 mAb was located on the surfaces of NB4 and THP-1 cells. The intensity of the DAB stain on NB4 cell surface was much higher than that on THP-1 cell surface, correlating with the mean fluorescence intensities (MFIs) in FACS assays (FIG. 1A, left panel).

Figure 1C:
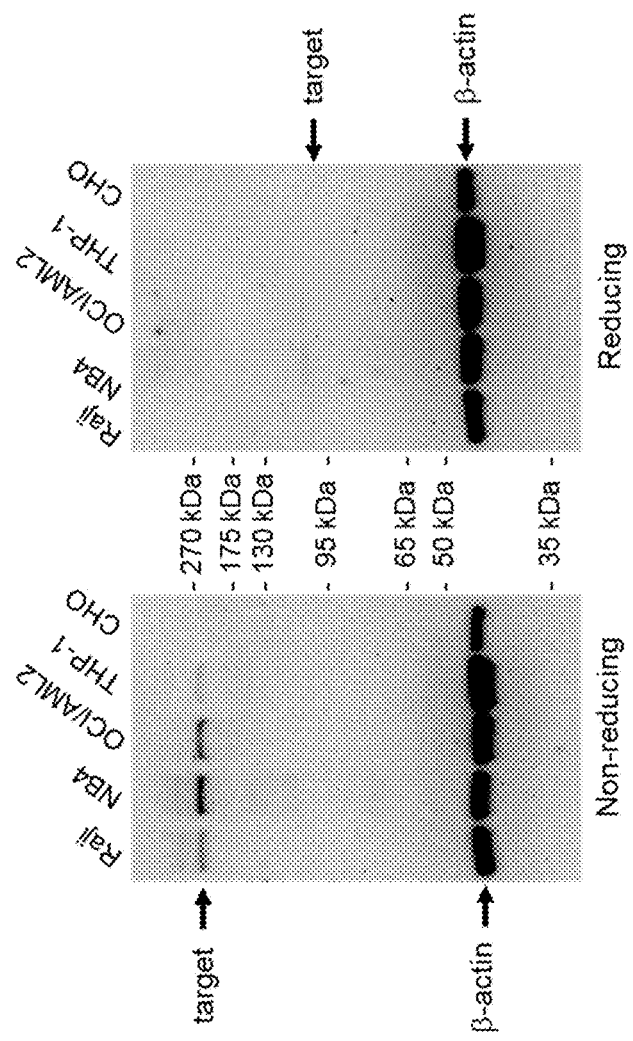

Moreover, Western blot of multiple AML cell lysates simultaneously probed by 5 µg/mL each of MAb11-22.1 mAb and mouse anti-human/mouse β-actin mAb (anti-β-actin mAb, Proteintech Group, Rosemont, Ill.), followed by detection with 1:20,000 dilution of anti-Mo IgG Fc-HRP pAb showed a common band of approximately 250 kDa under a non-reducing condition and a faint band of approximately 110 kDa under the reducing condition (FIG. 1C). The whole cell lysate of Raji, an acute lymphocytic leukemia (ALL) cell line, also showed blots in the same positions albeit with low intensities. In contrast, MAb11-22.1 mAb could not detect any band in Chinese hamster ovary (CHO) cells (FIG. 1C) or human PBMC cell lysate (data not shown) by Western blot. The relative intensities of these hybridized protein bands in the AML cells were consistent with the MFIs in FACS assays (FIG. 1A) and the intensities of ICC staining (FIG. 1B), implicating that this protein is likely the target of MAb11-22.1 mAb.

Example 2

Figure 2A:
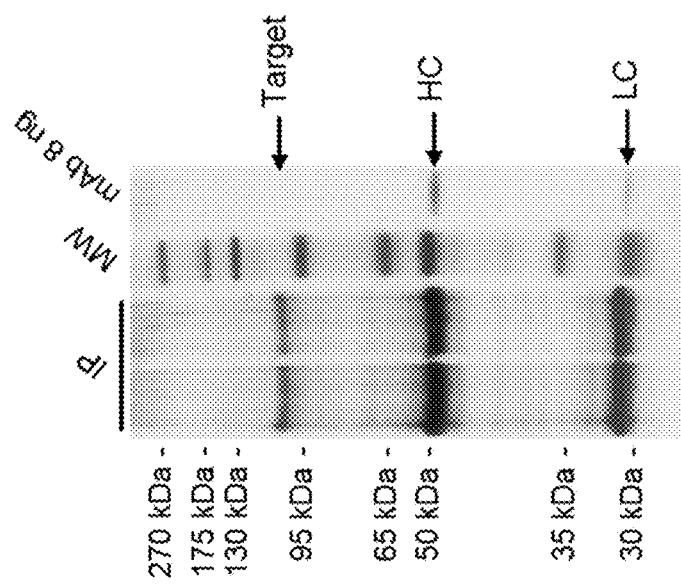
FIGS. 2A to 2D show the identification and confirmation of transferrin receptor 1 (TfR1) as the target of MAb11-22.1 mAb.

Identification and Verification of Human Transferrin Receptor 1 (TfR1) as the Target of MAb11-22.1 mAb The AML cell lysates were prepared with IP lysis buffer (Thermo Fisher Scientific) following the manufacturer's instruction. Dynabeads™ Protein-A for Immunoprecipitation (Thermo Fisher Scientific) was incubated with 50 µg MAb11-22.1 mAb or an isotype control Ab in PBS at room temperature (RT) for 30 minutes. The antibody-bound Dynabeads™ were washed and incubated with each cell lysate at RT for 30 minutes, and then washed sequentially with 0.5% TritonX-100/PBS and PBS buffer. The immunoprecipitated (IP) protein(s) and the antibody were separated from the beads with 4×Laemmli denaturing sample buffer with 2-mercaptoethanol and heated to 95° C. for five minutes. The proteins were separated by sodium dodecyl sulfate polyacrylamide gel electrophoresis (SDS-PAGE) and detected with ProteoSilver™ Silver Stain Kit (MilliporeSigma) following the manufacturer's protocol. A single protein band in the IP sample with the same molecular weight as that in Western blot was revealed by silver-staining (FIG. 2A). The band was excised from the gel and digested with trypsin. Liquid chromatography with tandem mass spectrometry (LC-MS/MS) performed by BGI Americas Corporation (Cambridge, Mass.) identified TfR1 as the most abundant protein in the gel slice (#PSM=32, coverage=29.6%).

Figure 2B:
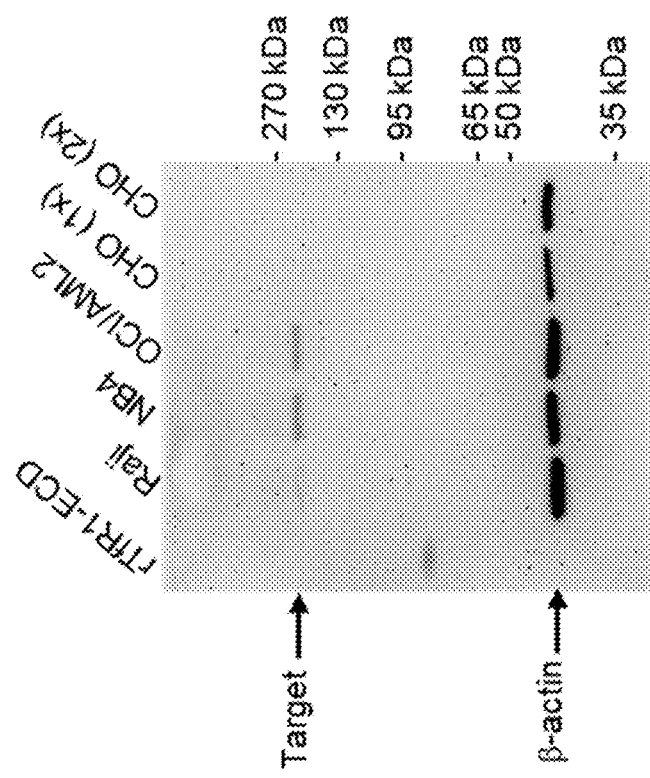

To confirm TfR1 as the target of MAb11-22.1 mAb, a recombinantly expressed human TfR1 extracellular domain with an N-terminal His tag (rTfR1-ECD, ACRO Biosystems, Newark, Del.), along with the whole cell lysate samples of AML and ALL cells (positive controls), and the CHO cell lysates (negative control), were analyzed by SDS-PAGE under non-reducing condition, followed by Western blot probed simultaneously with 5 µg/mL each of MAb11-22.1 mAb and anti-β-actin mAb as primary antibodies and 1:20,000 anti-Mo IgG Fc-HRP pAb (FIG. 2B). The result showed that MAb11-22.1 mAb could detect a single band of approximately 80 kDa that correlated with the calculated molecular weight of 77.0 kDa for rTfR1-ECD. The Raji, NB4, OCI/AML2 and CHO cell lysates showed consistent result in reaction with MAb11-22.1 mAb as in FIG. 1C.

Figure 2C:
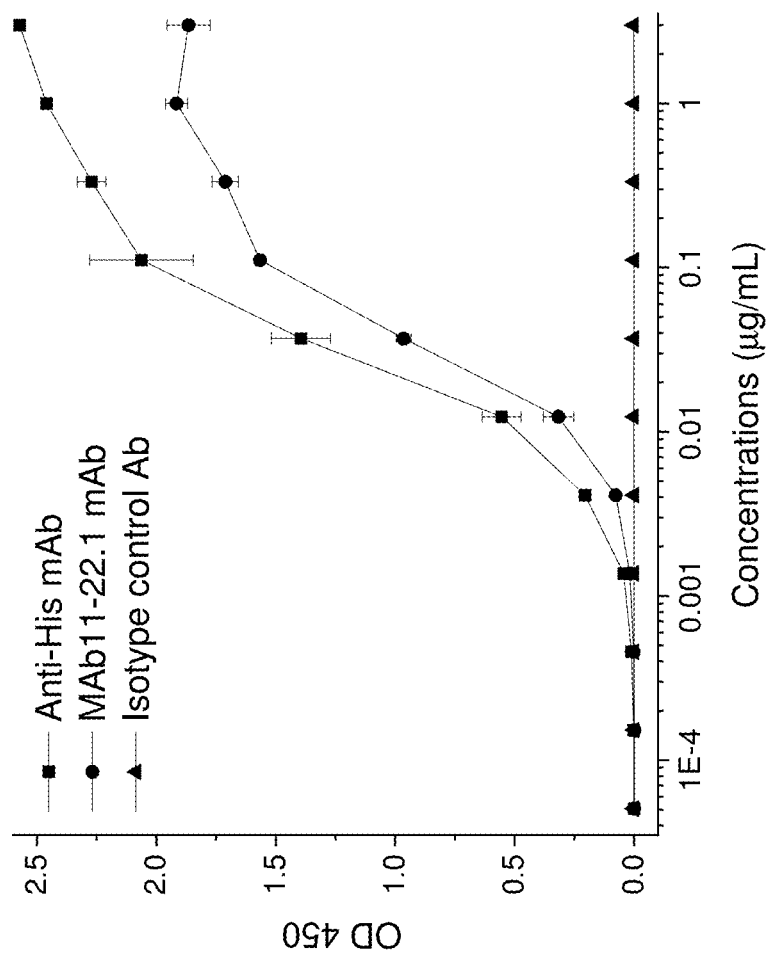

A direct ELISA assay was performed to verify the interaction between MAb11-22.1 mAb and rTfR1-ECD. Immulon® microtiter plates (Thermo Fisher) coated with 0.1 µg/mL rTfR1-ECD were reacted directly with MAb11-22.1 mAb, 6*His His-Tag monoclonal antibody (anti-His mAb, Proteintech), or the isotype control Ab in serial dilutions for one hour at RT, followed by reaction with 1:2,000 anti-Mo IgG Fc-HRP pAb for one hour. 3,3',5,5'-Tetramethylbenzidine (TMB) substrate was added and absorbance at 450 nm of wavelength was measured using a SpectraMax microplate reader (Molecular Device, San Jose, Calif.). FIG. 2C illustrates the direct interaction between 6His-tagged rTfR1-

ECD with MAb11-22.1 mAb or anti-His mAb, but not with the isotype control Ab, demonstrating that TfR1 was the target of MAb11-22.1 mAb.

Figure 2D:
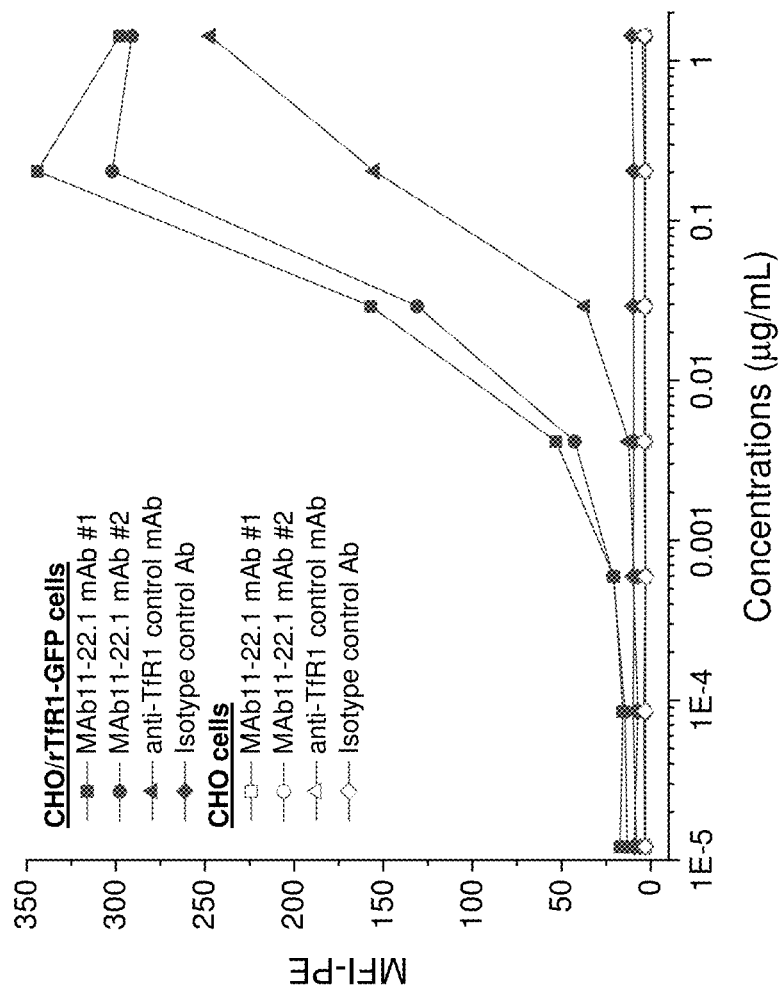

To further confirm that MAb11-22.1 mAb recognize human TfR1, TFRC, the cDNA encoding the full-length TfR1 protein, was amplified from the OCI/AML2 and THP-1 cells by reverse transcription-polymerase chain reaction (RT-PCR) using a pair of primers (SEQ ID NO: 11 and SEQ ID NO: 12) ordered from Integrated DNA Technologies (Coralville, Iowa). The cDNA was in-frame fused with a GFP-coding DNA fragment to its C-terminus and then cloned into an in-house expression vector containing the human CMV promoter and a puromycin resistant gene (PuroR) for selection. CHO-DG44 cells that were not stained by MAb11-22.1 mAb in FACS were transfected with the TFRC-GFP expression plasmid and grown in EX-CELL® CD CHO serum-free medium (SFM) supplemented with puromycin. CHO cell colonies stably expressing high-level EGFP were isolated and subcloned. At 4° C., CHO/rTfR1-GFP cells were stained with two batches of purified MAb11-22.1 mAb, anti-human TfR1 control mAb (R&D Systems, Minneapolis, Minn.), and the isotype control Ab for 30 minutes, followed by detection with R-Phycoerythrin (PE) AffiniPure Goat Anti-Mouse IgG (subclasses 1+2a+2b+3), Fcγ Fragment Specific pAb (anti-Mo IgG Fc-PE, Jackson ImmunoResearch). The result showed that in FL1 (GFP) gating, CHO/rTfR1-GFP cells were stained by both MAb11-22.1 mAb and anti-TfR1 control mAb, whereas either antibody could bind to CHO cells without rTfR-GFP expression on cell surface (FIG. 2D). The $IC_{50}$ value of MAb11-22.1 mAb was 0.03-0.04 μg/mL, much lower than that of anti-TfR1 control mAb, which was approximately 0.1 μg/mL. Staining of CHO/rTfR-GFP cells with various GFP activities by MAb11-22.1 mAb revealed positive correlation between MFI-PE values and MFI-FITC values (data not shown), proving the direct interaction between MAb11-22.1 mAb and the extracellular domain of human TfR1.

```
Forward primer:
                                    (SEQ ID NO: 11)
5'-GAATGATGGATCAAGCTAGATCAGC-3'

Reverse primer:
                                    (SEQ ID NO: 12)
5'-CTCATGGAAGCTATGGGTATCAC-3'
```

Example 3

Measurement of Binding Affinity between MAb11-22.1 mAb and rTfR1-ECD

Figure 3A:
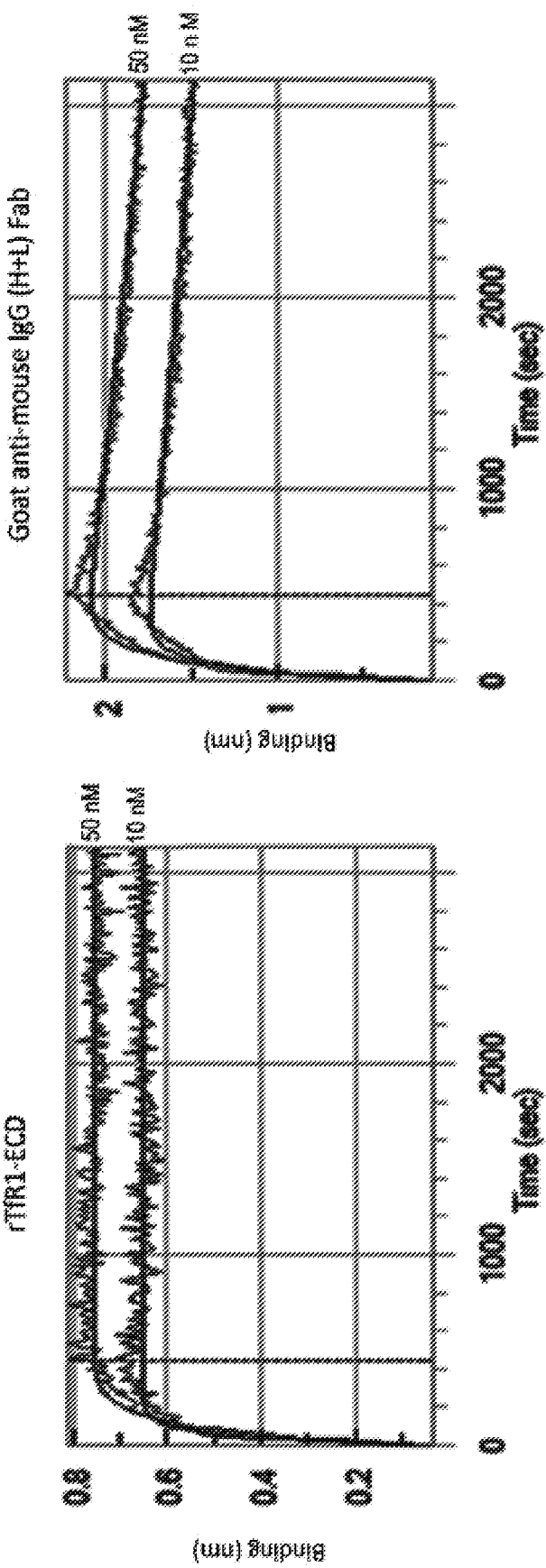

Bio-Layer Interferometry (BLI) label-free technology was used to determine the binding affinity between MAb11-22.1 mAb and the extracellular domain of TfR1 using the Octet® QK System (Molecular Devices, San Jose, Calif.). MAb11-22.1 mAb was immobilized to the Anti-Mouse IgG Fc Capture (AMC) biosensors for 450 seconds and washed with kinetics buffer for 120 seconds, followed by 450-second association with rTfR1-ECD in serial dilutions and then dissociation in kinetics buffer. Goat anti-mouse (H+L) Fab (Jackson ImmunoResearch) was used as a positive control in binding to MAb11-22.1 mAb. The assay was repeated multiple times using various concentrations of rTfR1-ECD from 300 nM down to 0.08 nM by serial dilution, but no signal decay was observed even if the dissociation time was extended to 60 minutes (FIG. 3A, left panel) or the reaction temperature was raised to 37° C. (data not shown). As a result, the interaction affinity between MAb11-22.1 mAb and rTfR1-ECD was extraordinarily high with a calculated $K_D$ value of <1 pM (FIG. 3B). Binding between MAb11-22.1 mAb and anti-mouse (H+L) Fab exhibited a regular kinetic curve (FIG. 3A, right panel) and a reasonably high affinity ($K_D$=1.04-1.45 nM) (FIG. 3C), indicating that the extremely high affinity between MAb11-22.1 mAb and rTfR1-ECD was not an artifact.

Example 4

Competitive ELISA of MAb11-22.1 mAb and Transferrin for Binding to Human TfR1

To determine if MAb11-22.1 mAb binds to human TfR1 overlapped the binding site of Tf, a competitive ELISA was performed. MAb11-22.1 mAb was labeled with HRP directly using EZ-Link Maleimide Activated HRP Kit (Thermo Fisher Scientific) following the manufacturer's instruction. An ImmunIon microtiter plate was coated with 0.1 μg/mL rTfR1-ECD and incubated for an hour with HRP-conjugated MAb11-22.1 mAb in four-fold dilutions starting from 2 μg/mL, that were individually mixed with human Tf (MilliporeSigma) by 2.5-fold serial dilutions starting from 2 μg/mL. Various concentrations of Tf were added alone as a negative control. Following thorough wash, TMB was added to detect binding of the HRP-conjugated MAb11-22.1 mAb. Absorbance at 450 nm was measured with SpectraMax microplate reader after adding the stopping solution.

Figure 4:
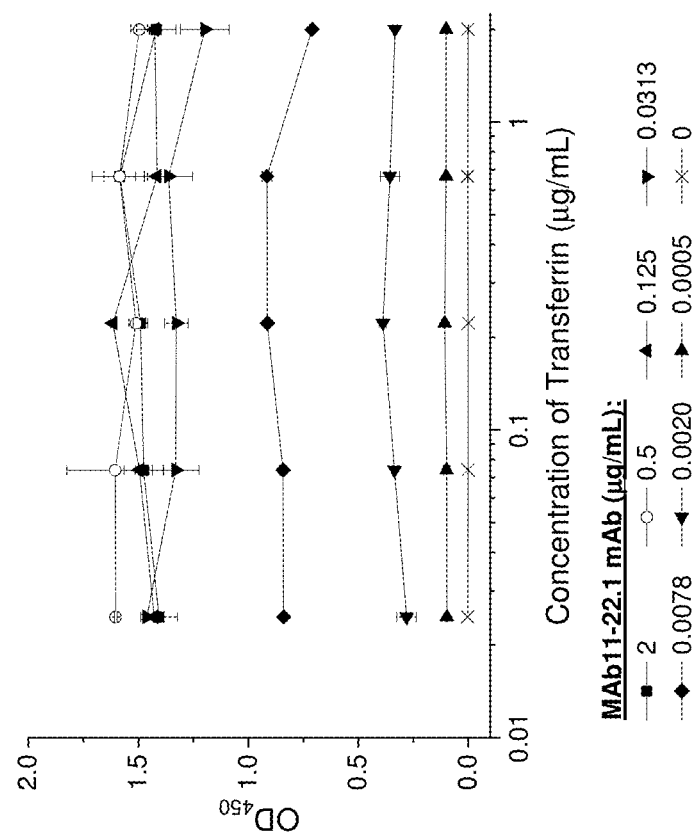
FIG. 4 is the competitive ELISA result revealing that MAb11-22.1 mAb and transferrin (TO bound to different sites on rTfR1-ECD. The ELISA plate was coated with 0.1 µg/mL of rTfR1-ECD and incubated with an array of five concentrations of the purified Tf protein (X axis) individually mixed with seven concentrations of four-fold serially diluted HRP-conjugated MAb11-22.1 mAb starting from 2 µg/mL, plus Tf alone at different concentrations. MAb11-22.1 mAb-HRP bound to rTfR1-ECD in a dose-dependent manner, but was independent of the presence of Tf. Data represent mean±standard deviations (SD) of duplicated samples.

FIG. 4 illustrates dose-dependent binding of MAb11-22.1 mAb-HRP to rTfR1-ECD that was independent of the presence of Tf after various concentrations. Addition of up to 2 μg/mL (25 μM) Tf did not significantly interfere with MAb11-22.1 mAb-HRP binding to rTfR1-ECD, suggesting that the binding site of Tf did not overlap with the epitopes of MAb11-22.1 mAb.

Example 5

FACS Analysis of MAb11-22.1 mAb on Binding to PBMC and Bone Marrow (BM) Cells

Other investigators showed that most anti-TfR1 antibodies interfered with Tf uptake and caused systemic hematologic toxicities, including anemia, neutropenia and leukopenia, in patients (CANDELARIA et al. Front. Immunol. 17 Mar. 2021). To address the safety issue of MAb11-22.1 mAb as a therapeutic candidate, multiple batches of fresh PBMC from healthy donors were purchased from Stanford Blood Center (Palo Alto, Calif.), while frozen BM cells from healthy donors or AML patients were purchased from HumanCells Bioscience (Fremont, Calif.). The cells were washed with PBS and blocked with ice-cold PBS and 1% bovine serum albumin (BSA). MAb11-22.1 mAb and the isotype control Ab in serial dilutions starting from 20 μg/mL were used to stain these cells at 4° C. followed by detection with 1:800 FITC- or PE-conjugated goat anti-Mo IgG Fc pAb (Jackson ImmunoResearch). In addition, anti-human CD34-FITC (REAL487), anti-human CD233-PE (REA368) and anti-human CD235a-PE (REA1092) were purchased from Miltenyi Biotec (San Jose, Calif.) to simultaneously stain the cells with MAb11-22.1 mAb.

Figure 5A:
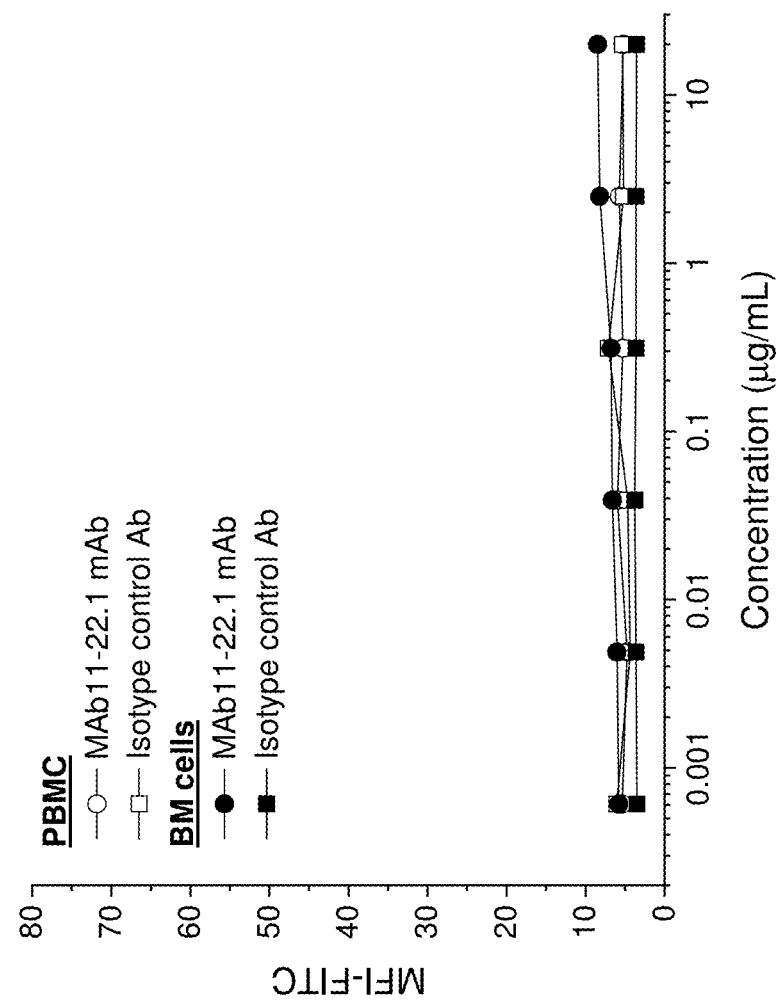
Figure 5B:
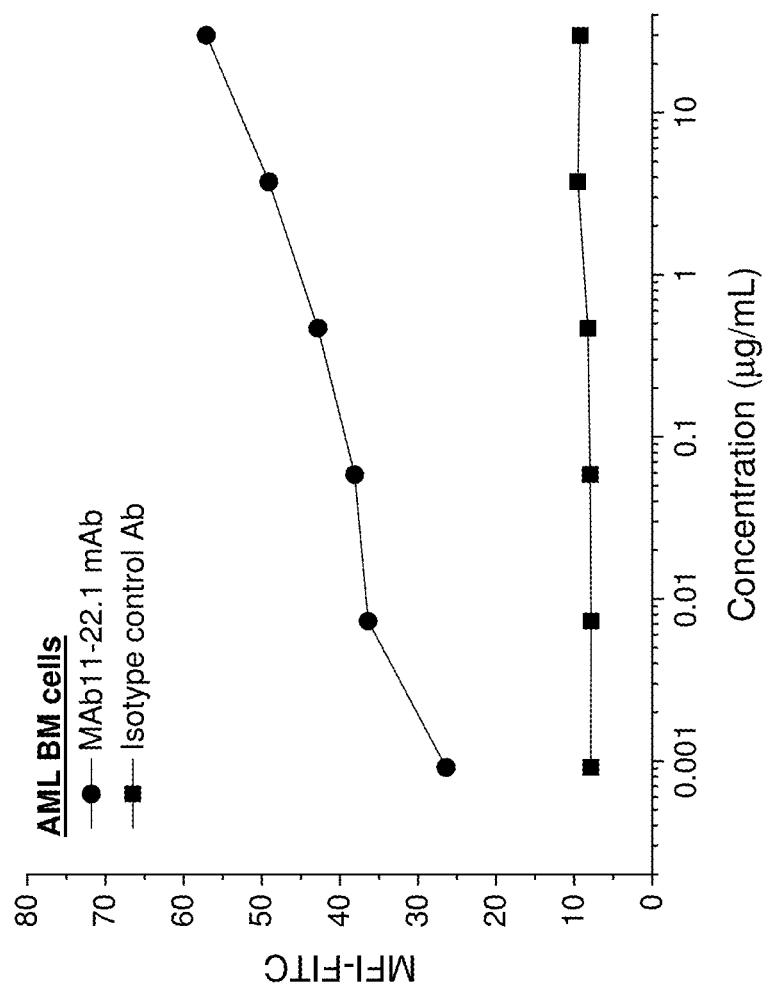
Figure 5E:
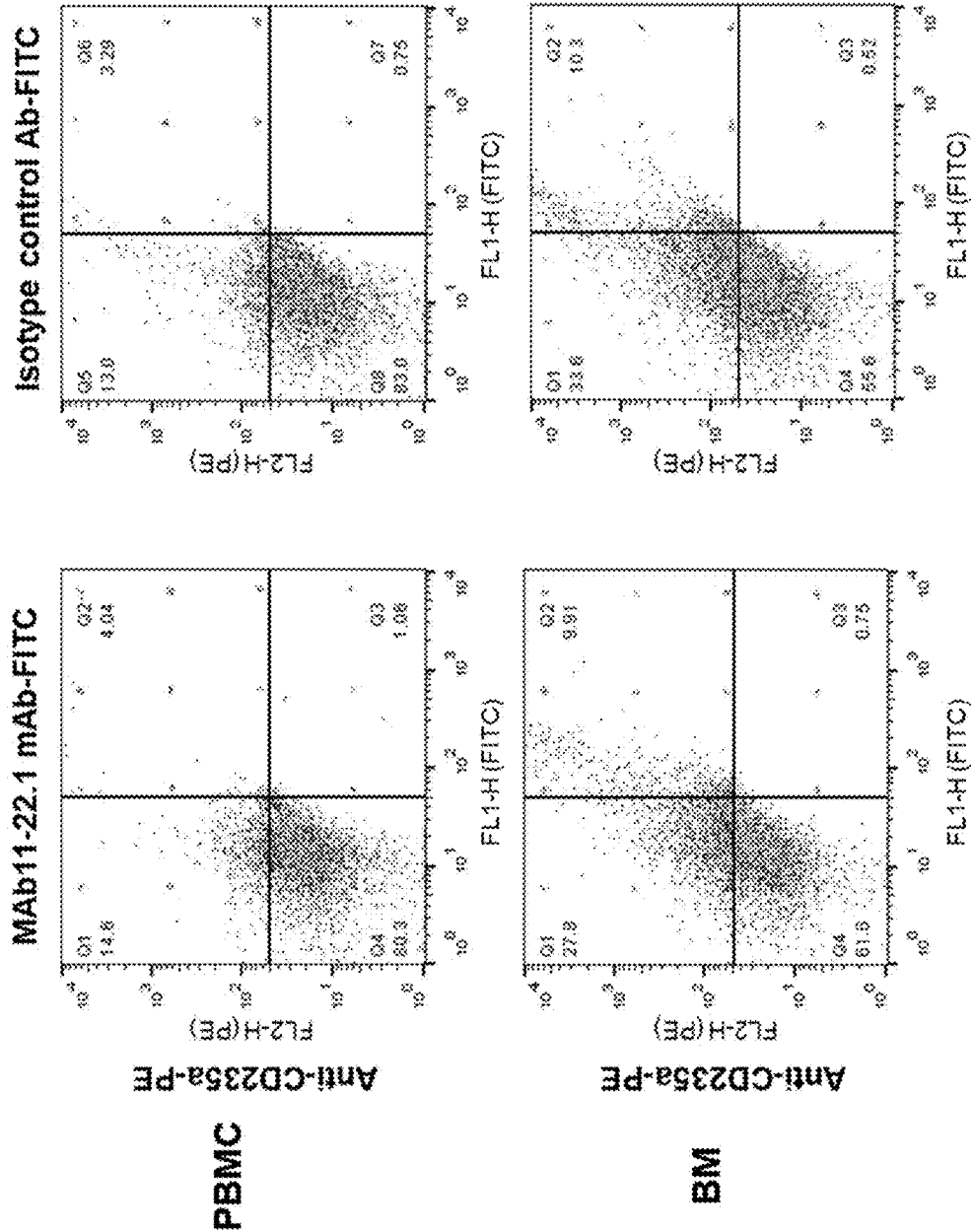
FIG. 5E shows that the erythrocytes and erythroblasts present in PBMC or BM cell clusters that were stained by anti-human CD235a-PE (Miltenyi) were not reactive with MAb11-22.1 mAb or the isotype control Ab.

The FACS results showed that MAb11-22.1 mAb did not bind to normal PBMC or normal BM cells regardless of the mAb concentrations used (FIG. 5A). Consistent results were obtained with different batches (donors) of PBMC and BM cells (data not shown). By contrast, the BM cells from an AML patient was reactive by MAb11-22.1 mAb but not the isotype control Ab (FIG. 5B), suggesting that MAb11-22.1 mAb could discriminate healthy BM from AML BM species. In healthy BM samples, over 20% cells were hematopoietic stem cells that could be stained by anti-human CD34 mAb-FITC (FIG. 5C left panels), but few were reactive with MAb11-22.1 mAb and the isotype control Ab (FIG. 5C middle and right panels). TfR1 is commonly considered as a marker for nucleated red blood cells, however, none of the CD233-positive erythrocytes or the CD235a-positive erythrocytes and erythroblasts was reactive with MAb11-22.1 mAb (FIGS. 5D and 5E, left panels), implicating that MAb11-22.1 mAb might only recognize TfR1 expressed on malignant cells and would have low risk to cause bone marrow suppression.

Example 6

Internalization Assays of MAb11-22.1 mAb by Tumor Cells

OCI/AML2, NB4 or Raji cells in DMEM supplemented with 10% Gibco Fetal Bovine Serum (FBS, Thermo Fisher Scientific) were plated at $1 \times 10^5$/well in two 96-well culture plates and co-incubated at 4° C. for an hour with MAb11-22.1 mAb, anti-CD20 mAb (R&D Systems) or isotype control mAb in a 1:10 serial dilution series, starting at 10 μg/mL. The cells were washed twice with ice-cold PBS by centrifugation at 500×g to remove the unbound mAbs. Cells in one 96-well plate were resuspended with warm culture medium and incubated at 37° C. to allow internalization of the mAb, whereas cells in another plate were resuspended in ice-cold culture medium and incubated at 4° C. to prevent antibody internalization. Samples taken at 30 minutes, one hour, and two hours were washed twice with ice-cold PBS/1% BSA, and subsequently incubated with 1:800 diluted anti-Mo IgG Fc-FITC for 30 minutes at 4° C. After washing three times with ice-cold PBS/1% BSA, the cells were resuspended in 150 μL of fixing solution containing 1% paraformaldehyde and stored in dark prior to FACS analysis.

Figure 6A:
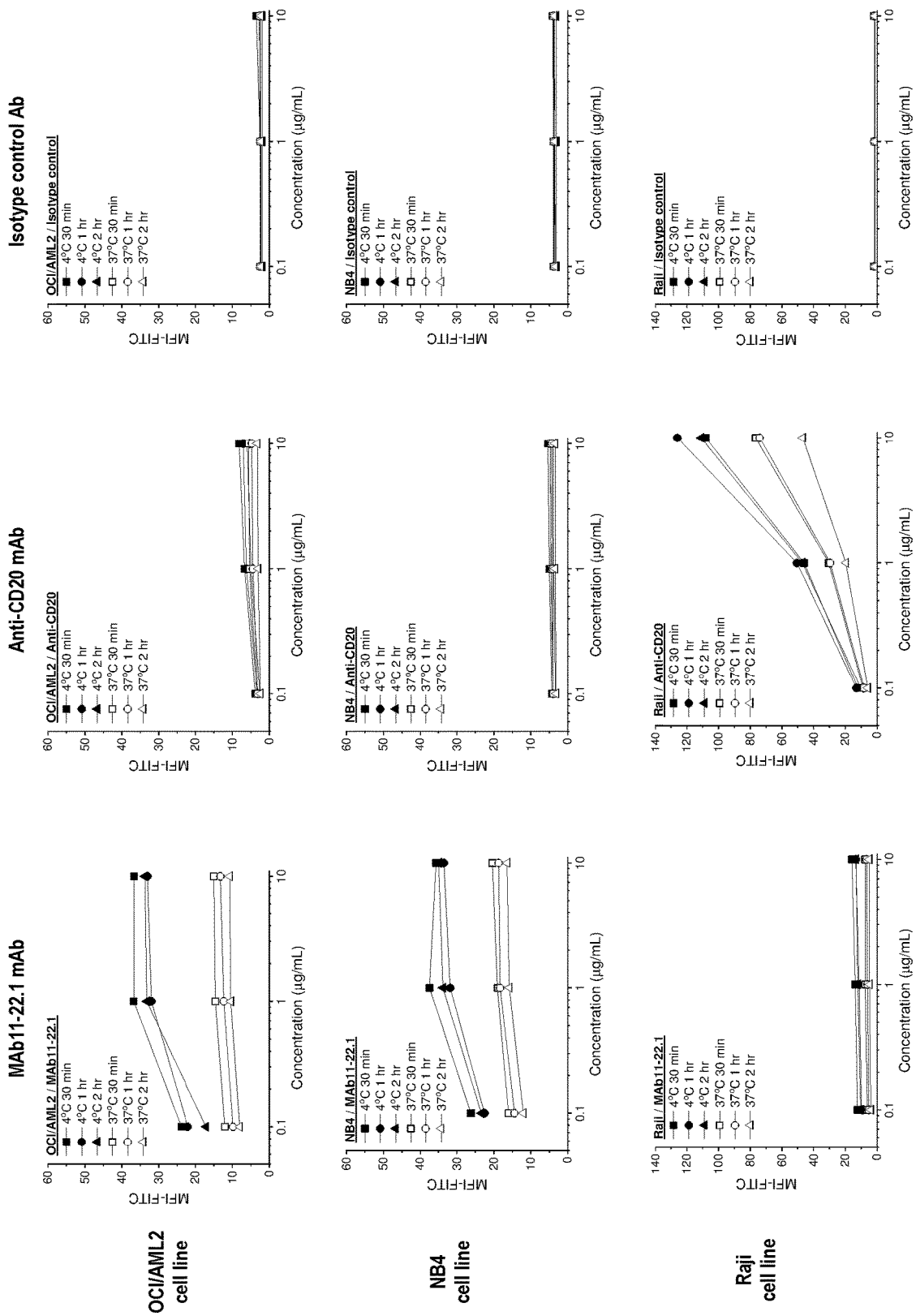
FIG. 6A to 6C are the internalization assay results of MAb11-22.1 mAb with cancer cell lines.

The FACS results showed that MAb11-22.1 mAb bound to the surfaces of the two AML cell lines, OCI-AML2 and NB4, in a dose-dependent manner at 4° C., but it was quickly internalized at 37° C. Although Raji cells seemed to have very low copy number of TfR1 on cell surface, they were still able to internalize MAb11-22.1 mAb at 37° C. (FIG. 6A left panels). On the contrary, the anti-CD20 mAb only bound to Raji cells but not the AML cells at 4° C., and it was partially internalized by Raji cells at 37° C. (FIG. 6A middle panels). The isotype control Ab did not stain any of the three cell lines as expected (FIG. 6A right panels).

FACS-based internalization assay could only provide indirect evidence of endocytosis of the antibody-antigen complexes and could not distinguish antibody internalization from antibody shedding. To directly observe mAb internalization, fluorescence microscope-based internalization analysis was performed using fluorescence-labeled mAbs. Briefly, mAbs were labeled with CF488 dye using Mix-n-Stain™ Antibody Labeling Kit (MilliporeSigma) following the manufacturer's protocol. Cell binding was carried out in 96-well culture plates with various mAb concentrations in ice-cold DMEM medium at 4° C. for one hour. After washing the cells twice with ice-cold PBS, one plate was incubated at 37° C. for another hour by adding warm DMEM, whereas cells in the other plate were resuspended in cold PBS for fluorescence imaging using Keyence BZ-X800 All-in-one Fluorescence Microscope (Keyence, Itasca, Ill.). The isotype control Ab was labeled with CF488 and incubated with the cells in parallel as a negative control.

Figure 6B:
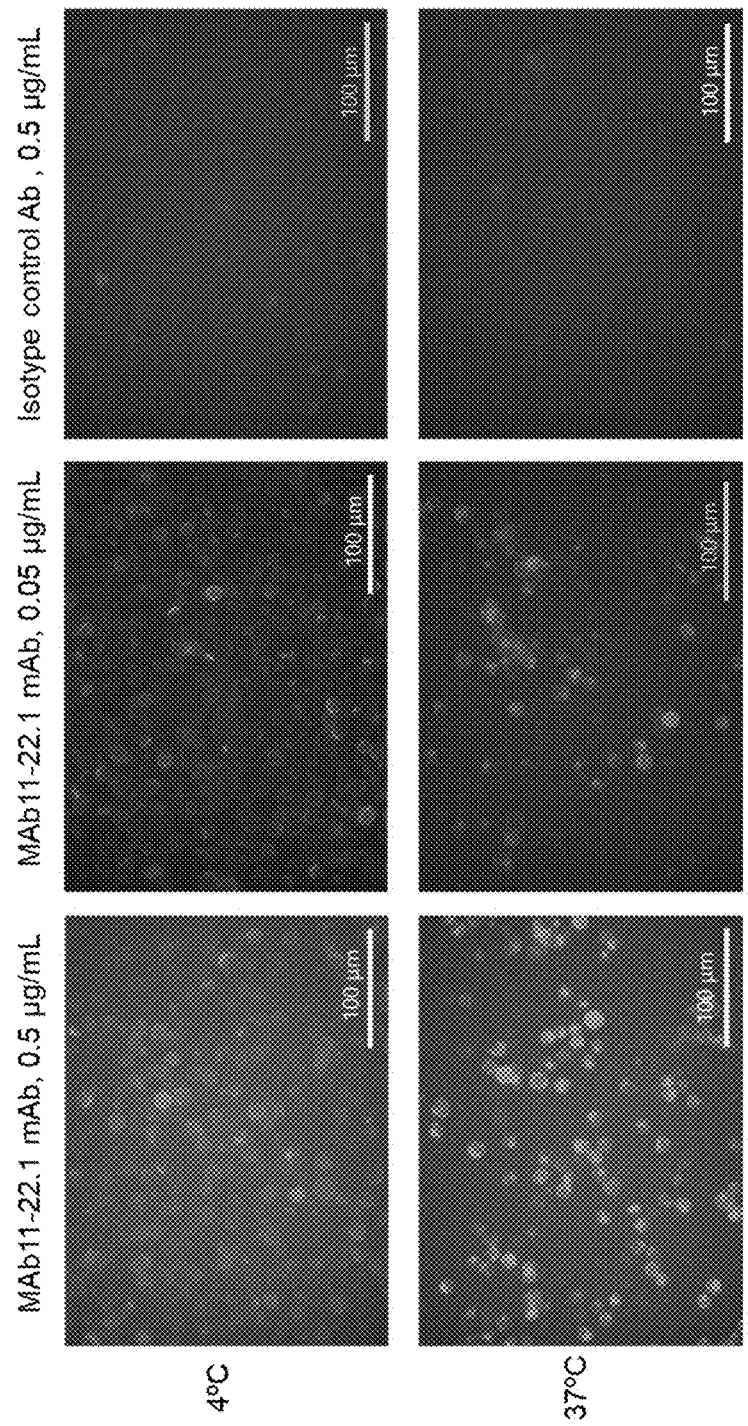

After one-hour incubation at 4° C., MAb11-22.1 mAb-CF488 was found to bind to the surface of OCI/AML2 cells, forming high-intensity fluorescence rings outlining the cells (FIG. 6B, upper panels). The fluorescence intensities were proportional to the concentrations of the mAb used. After one-hour incubation at 37° C., majority of the fluorescent signals shifted from cell surfaces to the inner space of the cells, suggesting that the surface-bound MAb11-22.1 mAb-CF488 molecules were mainly internalized by OCI/AML2 cells (FIG. 6B, lower panels). This phenomenon was consistently observed with different concentrations (1, 0.5, 0.1, and 0.05 μg/mL) of MAb11-22.1 mAb-CF488 in other AML cell lines, including NB4 and THP-1 (data not shown). The CF488-labeled isotype control Ab did not bind to any cell test (FIG. 6B, right panels).

Figure 6C:
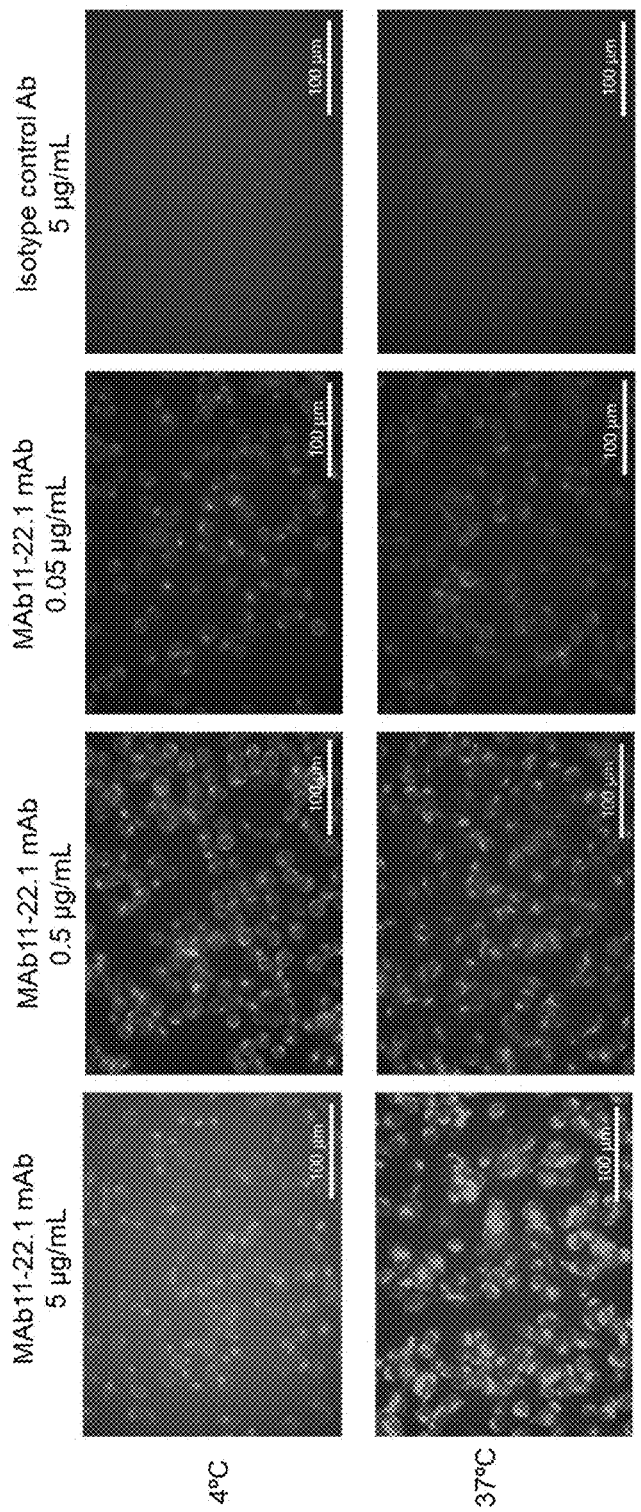

Similar dose-dependent binding and internalization results were observed with MDA-MB-231 cells, a triple-negative breast cancer (TNBC) cell line, which reacted strongly with MAb11-22.1 mAb at 4° C. as revealed by FACS analysis. However, the fluorescent signals in MDA-MB-231 cells were much stronger than those of AML cells as expected (FIG. 6C). In addition, partial internalization occurred even at 4° C. and the majority of MAb11-22.1 mAb-CF488 molecules were internalized after one-hour incubation at 37° C., suggesting that the TfR1 proteins expressed on MDA-MB-231 cell membrane had higher tendency to be internalized upon binding with MAb11-22.1 mAb.

Example 7

In Vitro Effect of MAb11-22.1 mAb on Proliferation of AML Cell Lines

The effect of MAb11-22.1 mAb on the proliferation of AML cell lines was evaluated with cell-based in vitro assays. The Cell Counting Kit-8 (CCK-8, Dojindo Molecular Technologies, Rockville, Md.) was used to determine cell viability following the manufacturer's protocol. Briefly, AML cells grown in DMEM/10% FBS and 100 μg/mL MAb11-22.1 mAb or isotype control Ab were seeded at $5 \times 10^3$ cells/well in triplicate in seven 96-well cell culture plates and incubated under a 5% $CO_2$ humidified atmosphere at 37° C. Cell viability was evaluated every 24 hours by incubation with 10 μL/well of CCK-8 solution for four hours followed by measurement of $OD_{450}$.

Figure 7:
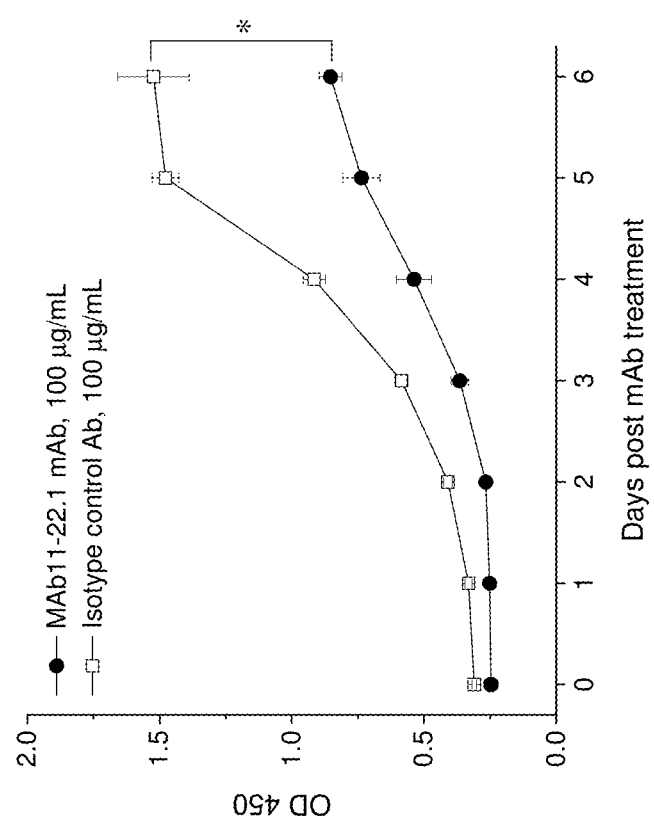
FIG. 7 illustrates the partial inhibitory effect of MAb11-22.1 mAb on the proliferation of OCI/AML2 cells. Cells ($2 \times 10^4$ cells/mL) were cultured in the presence of 100 μg/mL MAb11-22.1 mAb or isotype control Ab in humidified 5% $CO_2$ atmosphere at 37° C. Cell survival reflected by absorbance at 450 nm (OD450) was monitored every 24 fours by 4-hour treatment with 10 μL of CCK-8 solution. Data represent mean±SD of triplicated samples. *P<0.05.

As shown in FIG. 7, OCI/AML2 cells in both groups continued to grow, but the proliferation rate of the MAb11-22.1 mAb-treated cells was much lower than that of the cells treated with isotype control Ab ($P<0.05$). Similar data were obtained with other AML cell lines (data not shown). Therefore, although MAb11-22.1 mAb could partially inhibit the proliferation of OCI/AML2 cells, the mAb itself was not a robust therapeutic candidate. In fact, MAb11-22.1 mAb did not show any effect in a preliminary in vivo study involving a CLDX mouse model. Since MAb11-22.1 mAb had extremely high affinity with human TfR1 and showed strong tendency of internalization by cancer cells, it showed great potential to be developed into an ADC for cancer therapy.

Example 8

Sequencing of the Variable Region cDNA of MAb11-22.1 Hybridoma

The cDNAs encoding the variable regions of the light chain (VL) and heavy chain (VH) of MAb11-22.1 mAb were amplified from the total RNA of the MAb11-22.1 hybridoma cells by 5'-Rapid Amplification of cDNA Ends (5'-RACE) technique using SMARTer RACE 5'/3' Kit (Takara Bio USA, San Jose, CA). The primers for 5' -RACE are shown as SEQ ID NO: 13 and SEQ ID NO: 14. The cDNA fragments were amplified with Q5® High-Fidelity DNA Polymerase and cloned into the pMiniT2.0 vector (New England Biolabs, Ipswich, MA) following the manufacturer's protocol. Ten E. coli colonies of each transformant were randomly selected for plasmid purification with Hi-Speed Mini Plasmid Kits (IBI Scientific, Dubuque, Iowa) and Sanger DNA sequencing (Genewiz, South San Francisco, CA). All the sequences were verified by BLAST search at https://blast.ncbi.nlm.nih.gov/Blast.cgi and the international ImMunoGeneTics (IMGT) information system® (http://www.imgt.org) for the uniqueness of the V domains. Consensus sequences of VL and VH of MAb11-22.1 mAb are shown in the SUMMARY section as SEQ ID NO: 1 and SEQ ID NO: 3, respectively. The encoded amino acid sequences are shown as SEQ ID NO: 2 and SEQ ID NO: 4, respectively.

```
Light chain primer:
                                (SEQ ID NO: 13)
5'-CTGCTCACTGGATGGTGGGAAGATGG-3'

Heavy chain primer:
                                (SEQ ID NO: 14)
5'-AGCTGGGAAGGTGTGCACAC-3'
```

Construction and Expression of Chimeric MAb11-22.1 Ab (cAb)

The VL and VH genes of MAb11-22.1 mAb were PCR amplified from the sequenced plasmids using primer pairs shown as SEQ ID NO: 15 to 18 below. The PCR fragments were digested with SpeI-NarI (VL) or XbaI-NheI (VH) restriction enzymes (New England Biolabs) and ligated in-frame with the constant regions of human kappa light chain (CL) or human IgG1 heavy chain (CH1-CH3), respectively, carried in an in-house expression vector that contained the mouse CMV promoter and the human CMV IE1 promoter to control the expression of light chain and heavy chain, respectively.

```
LV PCR Forward primer:
                                (SEQ ID NO: 15)
5'-AGCACTAGTGCCGCCACCATGGAATCACAGACTCAGG-3'

LV PCR Reverse primer:
                                (SEQ ID NO: 16)
5'-CTGGGCGCCGCTACAGTCCGTTTCAGCTCCAGCTTGG-3'

HV PCR Forward primer:
                                (SEQ ID NO: 17)
5'-AGCTCTAGAGCCGCCACCATGGAGACAGACACACTCCTG-3'

HC PCR Reverse primer:
                                (SEQ ID NO: 18)
5'-GCCTTTGGTGCTAGCAGAGACAGTGACCAGAGTC-3'
```

After confirmation by DNA sequencing, the expression plasmid was transfected into Dux-1S-HD cells, an in-house developed CHO-DG44 derivative that could grow to high density in EX-CELL® CD CHO SFM, using FectoPro transfection reagent (Polyplus-Transfection® SA, Illkirch, France) following the manufacturer's instruction. Transient expression and secretion of MAb11-22.1 cAb in EX-CELL® CD CHO SFM was verified by FACS analysis for binding to AML cell lines followed by affinity purification with MabSelect™ SuRe™ Protein A resin (GE Healthcare).

Example 9

Characterization of MAb11-22.1 cAb

Figure 8A:
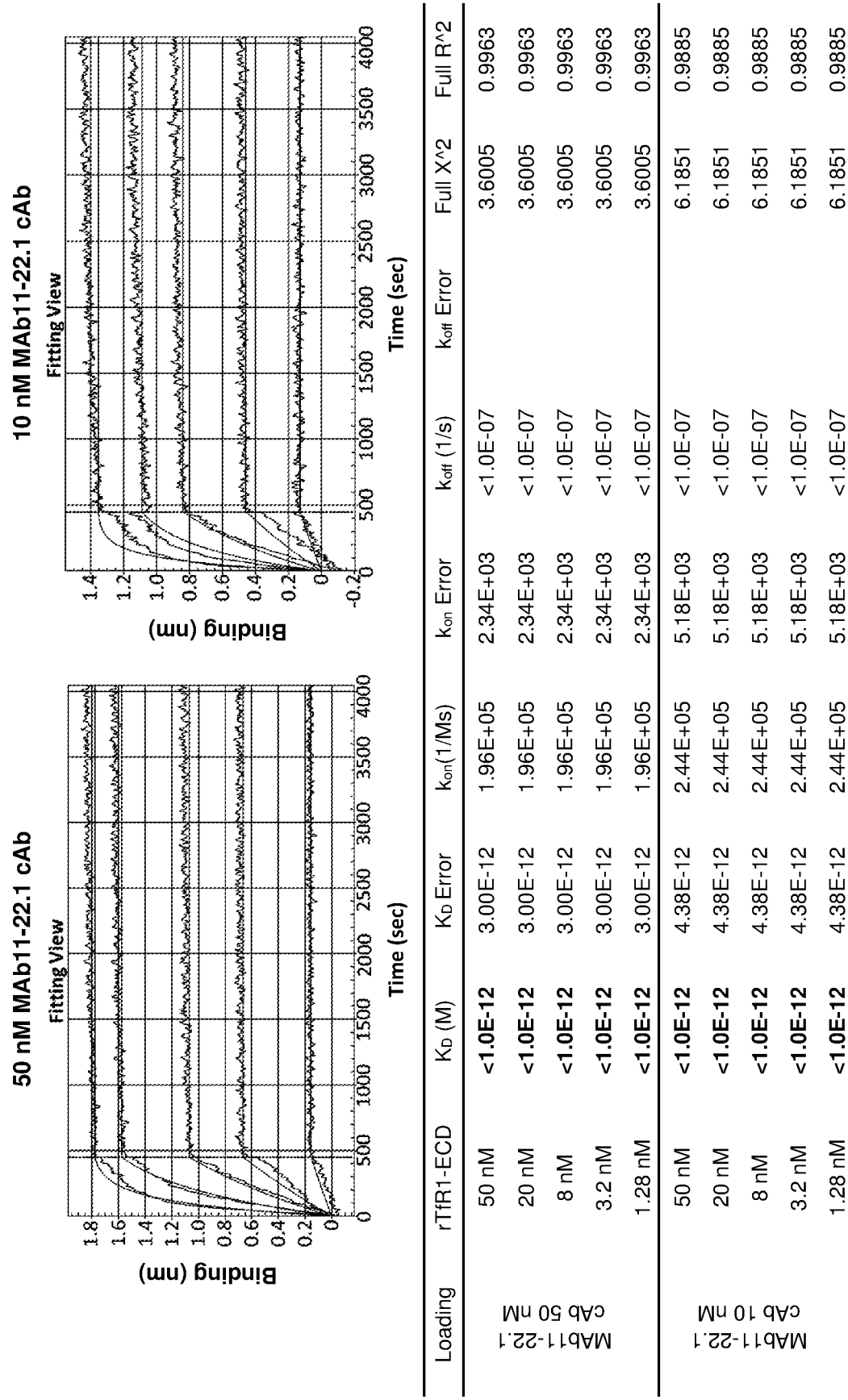
FIGS. 8A and 8B are data output from the ForteBio Octet® QK System showing the affinity and kinetics between MAb11-22.1 chimeric Ab (cAb) and rTfR1-ECD.
Figure 8B:
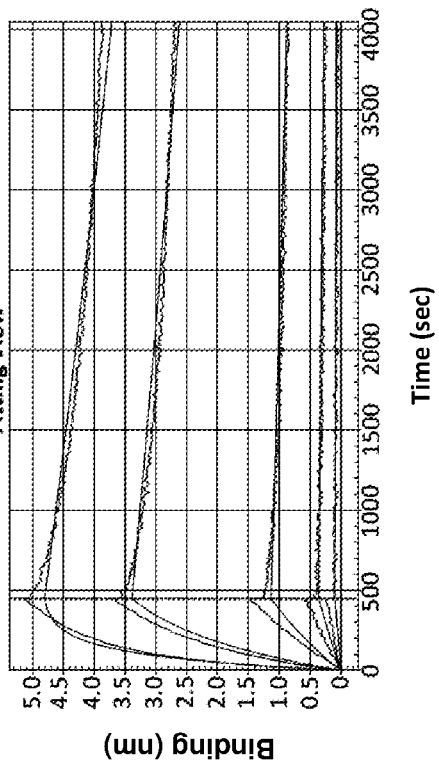

The purified cAb showed similar features as its mAb counterpart in assays such as SDS-PAGE, ELISA, and FACS (data not shown). The binding kinetics between MAb11-22.1 cAb and rTfR1-ECD was also determined by Octet® QK System. Anti-Human IgG Fc Capture (AHC) biosensors were used to immobilize MAb11-22.1 cAb for 450 seconds, and goat anti-human (H+L) Fab (Jackson ImmunoResearch) was used as a system control in binding to MAb11-22.1 cAb. Concentrations of rTfR1-ECD ranged from 50 nM to 1.28 nM by 2.5-fold serial dilutions. As for the MAb11-22.1 mAb shown in FIG. 3A to 3C, the dissociation ($K_{off}$) of MAb11-22.1 cAb was not detectable within 60 minutes of observation and therefore, the affinity between MAb11-22.1 cAb and rTfR1-ECD was extremely high ($K_D$<1 pM, FIG. 8A). Binding between MAb11-22.1 cAb and Anti-human (H+L) Fab exhibited a regular kinetic curve with $K_D$ of 2.18 nM as expected (FIG. 8B).

Example 10

In Vitro Effect of MAb11-22.1-S239C-DM1 on Cancer Cell Lines

Even though MAb11-22.1 mAb did not have strong cytotoxic activity, its extraordinarily high affinity with human TfR1 and high tumor specificity made it a good ADC candidate for the treatment of cancer. To investigate whether it could be applied as an ADC agent, Cysteine scanning was carried out on the surface exposed residues of the light chain and heavy chain constant regions of MAb11-22.1 cAb to explore anti-tumor effect by site-specific conjugation of various payloads. Site-directed mutagenesis replaced the Serine 239 codon (TCC) with a Cysteine codon (TGC) in the heavy chain Fc region of MAb11-22.1 cAb using primer pairs shown as SEQ ID NO: 19 and 20 below. The MAb11-22.1-S293C cAb variant was transiently expressed and purified using MabSelect™ SuRe™ Protein A resin. The cysteine or glutathione present in culture medium that bound to Cys239 of MAb11-22.1-5293C cAb was removed by treatment with 10-fold molar excess dithiothreitol (DTT) in PBS at room temperature as described by JUNUTULA et al. (Nat Biotechnol. 26:925-932, 2008). The antibody was refolded to expose the free thiol groups of S239C and the integrity of cAb was analyzed by SDS-PAGE. Site-specific conjugation was carried out by reaction between the free thiol groups of Cys239 and DM1 in PBS with slow stirring at room temperature for 10 to 60 minutes to generate MAb11-22.1-S293C-DM1, which conferred ADC activity with a theoretical drug-to-antibody ratio (DAR) of 2. Free DM1 was removed by diafiltration against a ten-fold volume of PBS three times using an Amicon® Stirred Cell Reservoir equipped with a 30-kDa NMW Ultrafiltration Disc (MilliporeSigma). MAb11-22.1-S293C-DM1 was then filter-sterilized with a 0.2 µm syringe filter (VWR International, Radnor, Pa.). unmutated MAb11-22.1 cAb and isotype control Ab were also treated with DM1 in parallel as negative controls to exclude the effect caused by non-site-specific conjugation. The integrity and binding capacity of the DM1-treated antibodies were analyzed by SDS-PAGE, ELISA, and FACS. Endotoxin was analyzed with Pierce™ Chromogenic Endotoxin Quant Kit (Thermo Fisher). No apparent difference was observed between MAb11-22.1 cAb-DM1 and MAb11-22.1-S239C-DM1 in binding affinity to TfR1 and cancer cell lines. As expected, MAb11-22.1-S239C-DM1 showed minor retardation of in-gel migration in comparison with the un-treated MAb11-22.1-S239C.

```
S239C Forward primer:
                                            (SEQ ID NO: 19)
5'-AACTCCTGGGTGGACCTTGCGTGTTTCTGTTCCCCCCTAAGC-3'

S239C Reverse primer:
                                            (SEQ ID NO: 20)
5'-AACACGCAAGGTCCACCCAGGAGTTCAGGAGCAGGGCAAGG-3'
```

Representative cancer cell lines, including OCI/AML2 (AML subtype M4), Raji (ALL), HCC38 (TNBC), and MDA-MB-231 (TNBC), were cultured in DMEM/10% FBS culture medium to log phase. On Day 0, an optimized amount of each cell line was mixed with individual antibodies in triplicate in 96-well cell culture plates to achieve a baseline $OD_{450}$ of approximately 0.4 in the CCK-8 assay. The cells were incubated at 37° C. with 5% $CO_2$ atmosphere. Cell proliferation was monitored on Day 3 and Day 5 by CCK-8 assay. The isotype control Ab without DM1 treatment reflected the baseline of cell proliferation. Both MAb11-22.1-S239C and MAb11-22.1 cAb with or without DM1 treatment were compared in this study.

Figure 9:
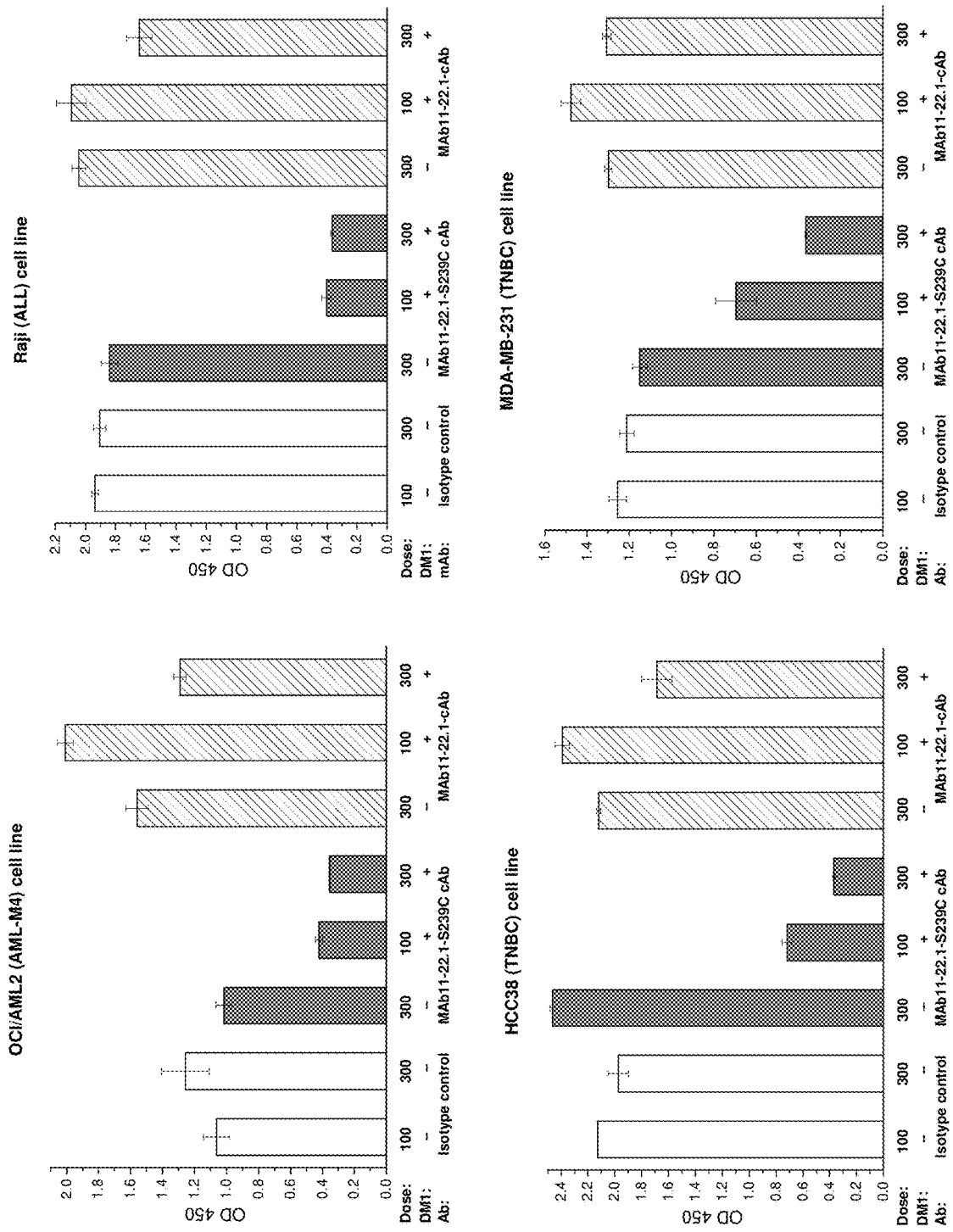
FIG. 9 are bar graphs illustrating the effect of MAb11-22.1 cAb with or without S239C mutation, and an isotype control Ab on the proliferation of a variety of cancer cell lines in vitro. The OCI/AML2, Raji, HCC38, and MDA-MB-231 cell lines in optimized amounts were cultured with individual antibodies for five days and then analyzed with the CCK-8 assay. Two doses (100 and 300 μg/mL) of MAb11-22.1 cAb (hatched bars) and MAb11-22.1-S239C cAb (gray bars) were treated with DM1, as indicated by "+" symbols under the X axis; antibodies without DM1 treatment were indicated by "—" symbols. The unconjugated isotype control Ab (white bars) reflected the baseline of proliferation of each cell line. Data represent mean±SD of triplicated samples.

As illustrated in FIG. 9, cell proliferation of all four cell lines were inhibited by MAb11-22.1-S239C-DM1, but not by the un-treated MAb11-22.1-S239C cAb. Wild-type MAb11-22.1 cAb had no apparent effect on cell proliferation regardless of DM1-treatment. The AML and ALL cell lines were highly sensitive to MAb11-22.1-S239C-DM1 as both 100 μg/mL and 300 μg/mL completely inhibited cell proliferation. The two TNBC cell lines were less sensitive to MAb11-22.1-S239C-DM1 since 100 μg/mL concentration only had partially inhibitory effects.

Example 11

Assessment of MAb11-22.1-S239C-DM1 In Vivo with an AML Xenograft Mouse Model

A xenograft model was established using nu/nu mice to evaluate the effect of MAb11-22.1-S239C-DM1 on AML tumor growth. Each male athymic nude mice aged 6 weeks (Charles River Laboratories, Wilmington, MA) was injected with $1.5 \times 10^6$ OCI/AML2 cells in 0.1 ml of PBS into the subcutaneous space of the right flank. When all tumor nodules were visible, the mice were randomly divided into three different groups (n=5 or 6) to be treated once every four days for seven times (Q4×7) by intraperitoneal (i.p.) injection of MAb11-22.1-S239C-DM1 (10 mg/kg b.wt for low dose or 20 mg/kg b.wt for high dose) or an isotype control Ab (no S239C mutation) that was also treated with DM1 (20 mg/kg b.wt). Tumor volumes and body weights were measured every four days immediately before drug administration. Tumor volumes were calculated using the formula: Volume=½×(width)²×length. Animals were euthanized when tumor volume exceeded 2000 $mm^3$ or if the tumor became necrotic or ulcerated through the skin.

Figure 10:
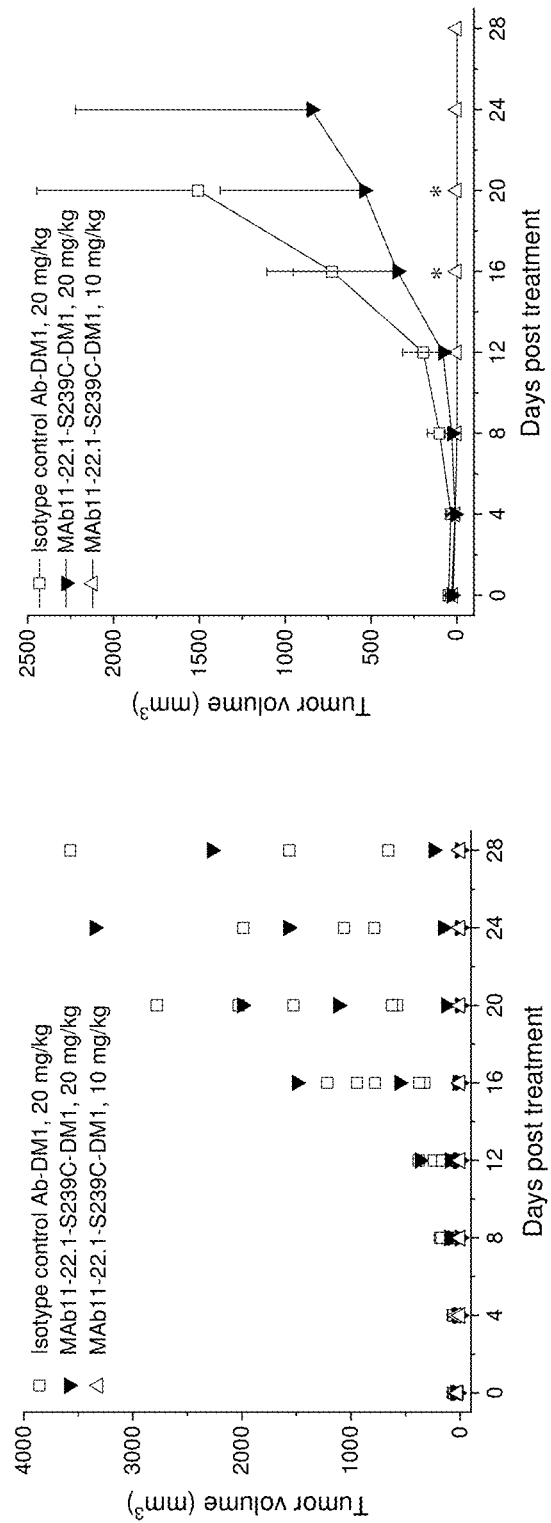
FIG. 10 shows the in vivo efficacy of MAb11-22.1-S239C-DM1 on tumor growth in the OCI/AML2 cell line-derived xenograft (CLDX) mouse model. MAb11-22.1-S239C-DM1 was injected into the intraperitoneal cavity (i.p.) at 10 mg/kg (low-dose, n=5) or 20 mg/kg (high-dose, n=6) in a Q4×7 schedule (Day 0 to 24). A negative control group was administrated with a DM1-treated isotype control Ab (no S239C mutation) at 20 mg/kg/Q4×7/i.p. (n=5). Tumor volumes were measured every four days. The left panel plots the tumor volume of individual mouse in each group and the right panel compares the mean tumor volume±SD between different groups. Starting on Day 16 after four Ab treatment, the mean tumor volume of the low-dose group was significantly different from that of the isotype control-DM1 group (*P<0.05).

The OCI/AML2 xenograft is an aggressive CLDX mouse model. Neither MAb11-22.1 mAb nor MAb11-22.1 cAb alone could markedly slow down the growth of the OCI/AML2 xenograft tumors (P>0.05, data not shown). In the current study, 10 mg/kg b.wt (low-dose) of MAb11-22.1-S239C-DM1 produced complete regressions and durable responses after one or two drug administrations (FIG. 10). Mice in the 20 mg/kg b.wt (high-dose) MAb11-22.1-S239C-DM1 treated group (n=6) showed variable responses: three mice had 100% reduction in tumor volume since Day 4 or Day 8 like the low-dose group; another mouse showed tumor regression on Day 4 and 8, but the tumor regrew thereafter; the remaining two mice did not respond to MAb11-22.1-S239C-DM1 and one was euthanized on Day 24 due to tumor progression. In the isotype control group (n=5), all tumors grew continuously, and two mice were euthanized on Day 20 because their tumors exceeded 2000 $mm^3$. Although very high doses of ADC were used, no systemic side effect, such as change in vital signs, loss of mobility, appetite, or total body weight, was observed during the study.

The effect of MAb11-22.1-S239C-DM1 on tumor growth was evident when compared with the isotype control group, confirming that MAb11-22.1 cAb could be a good candidate as ADC for cancer treatment. With high affinity and specificity to human TfR1, circulating MAb11-22.1-S239C could accumulate on TfR1-positive tumor cells and deliver DM1 intracellularly via endocytosis. In the presence of high concentration of Glutathione (GSH) in tumor cells, DM1 could be release from the ADC and confer by-stand killing effect to surrounding cells in xenograft tumor, implicating that MAb11-22.1 ADC could be applied not only in blood malignancies, but solid tumors as well.

The mechanism underlining the variable efficacy in the high-dose group remains obscure. It might contribute to the small sample size and individual variations in response to the compounds due to different expression levels of TfR1 on cell surface of tumors. Occasionally, high-dose ADC drug could be quickly cleared or induce drug resistance, and therefore, there should be an optimization of the dosing window for MAb11-22.1-S239C-DM1. Nevertheless, based on its high tumor specificity and anti-tumor potency data, MAb11-22.1 is an ideal anti-TfR1 antibody for the development of ADC. The conjugation technologies with potent payloads and ideal linkers for MAb11-22.1 ADC are currently under investigation to achieve consistent DAR and optimal dose window for cancer treatment.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "including", "containing", "having" and "have" are to be read as synonyms and expansively and without limitation. The methods and processes illustratively described herein suitably may be practiced in differing orders of steps, and that they are not necessarily restricted to the orders of steps indicated herein or in the claims.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

INCORPORATION BY REFERENCE

All patents and patent applications cited herein are hereby incorporated by reference, as are all other references cited.
Patents Mentioned:
In general on Abs:
U.S. Pat. No. 7,317,091B2
U.S. Pat. No. 5,500,362
U.S. Pat. No. 4,816,567
U.S. Pat. No. 5,225,539
U.S. Pat. Nos. 5,565,332; 5,580,717; 5,733,743; and 6,265,150;
U.S. Pat. No. 5,932,448
U.S. Pat. No. 7,538,196
U.S. Pat. No. 8,148,496
U.S. Pat. No. 8,518,891
U.S. Pat. No. 9,310,373
U.S. Pat. No. 9,764,041
U.S. Pat. No. 11,040,084
EP 239 400 B1
WO 00/53211 and U.S. Pat. No. 5,981,568
WO2014146487A1
US Publ'n No. 20170151343
US Publ'n No. 20170335281
WO2017114204
US Publ'n No. 20210139602 A1

Citations to Non-Patent Literature Cited in the Description by Name of Author(s) Only:

Bomford A B and Munro H N. Hepatology. (1985) 5:870-875.
Brooks D, Taylor C, Dos Santos B, Linden H, Houghton A, Hecht T T. Clin Cancer Res. (1995) 1:1259-1265.
Callens, C, Moura I C, Lepelletier Y, Coulon S, Renand A, Dussiot M, Ghez D, Benhamou M, Monteiro R C, Bazarbachi A, and Hermine O. Leukemia. (2008) 22:42-48.
Candelaria P V, Leoh L S, Penichet M L, and Daniels-Wells T R. Front. Immunol. 17 Mar. 2021. doi.org/10.3389/fimmu.2021.607692
Daniels T R, Delgado T, Rodriguez J A, Helguera G, and Penichet M L. Clin Immunol. (2006) 121:144-158.
Daniels T R, Ortiz-Sanchez E, Luria-Perez R, Quintero R, Helguera G, Bonavida B, Martínez-Maza O, and Penichet M L. J Immunother. (2011) 34:500-508.
Daniels-Wells T R, Candelaria P V, Emiko K, Wen J, Weng L, Kamata M, Almagro J C, Martínez-Maza O, and Penichet M L. Cancer Res. (2020) 80(16 Suppl):5655.
Daniels-Wells T R, Widney D P, Leoh L S, Martínez-Maza O, Penichet M L. J Immunother. (2015) 38:307-310.
Faulk W P, Hsi B L, Stevens P J. Lancet. (1980) 2:390-392.
Feng R, Wang Y, Ramachandran V, Ma Q, May M M, Li M, Zhou J X, Xu X, Xu K, Fang S, Xia W, Sui D, Liu H, Gao X, Prieto V, Blacklow S C, Lu M, Lee J E. J Exp Clin Cancer Res. (2020) 39:273.
Gatter K C, Brown G, Trowbridge I S, Woolston R E, Mason D Y. J Clin Pathol. (1983) 36:539-545.
Jeong S M, Hwang S, Seong R H. Biochem Biophys Res Commun. (2016) 471:373-379.
Johnson M, El-Khoueiry A, Hafez N, Lakhani N, Mamdani H, Rodon J, Sanborn R E, Garcia-Corbacho J, Boni V, Stroh M, Hannah A L, Wang S, Castro H, Spira A. Clin Cancer Res. (2021) 27:4521-4530.
Junutula J R, Raab H, Clark S, Bhakta S, Leipold D D, Weir S, Chen Y, Simpson M, Tsai S P, Dennis M S, Lu Y, Meng Y G, Ng C, Yang J, Lee C C, Duenas E, Gorrell J, Katta V, Kim A, McDorman K, Flagella K, Venook R, Ross S, Spencer S D, Lee Wong W, Lowman H B, Vandlen R, Sliwkowski M X, Scheller R H, Polakis P, Mallet W. Nat Biotechnol. (2008) 26:925-932.
Kohler & Milstein. Nature 1975; 256:495-497
Lepelletier Y, Camara-Clayette V, Jin H, Hermant A, Coulon S, Dussiot M, Arcos-Fajardo M, Baude C, Canionni D, Delarue R, Brousse N, Benaroch P, Benhamou M, Ribrag V, Monteiro R C, Moura I C, Hermine O. Cancer Res. (2007) 67:1145-1154.
Li M, Gao J, Feng R, Wang Y, Chen X, Sun J, Zhang D, Zhu Z, Ellis L M, Lu M, Lee J E, Feng Z, Liu B. PLoS One. 2013; 8:e77398
Moura I C, Centelles M N, Arcos-Fajardo M, Malheiros D M, Collawn J F, Cooper M D, Monteiro R C. J Exp Med. (2001) 94:417-425.
Moura, I. C., Y. Lepelletier, B. Arnulf, P. England, C. Baude, C. Blood. (2004) 103:1838-1845.
Nagai K, Nakahata S, Shimosaki S, Tamura T, Kondo Y, Baba T, Taki T, Taniwaki M, Kurosawa G, Sudo Y, Okada S, Sakoda S, Morishita K. Cancer Med. (2014) 3:1085-1099.
Neiveyans M, Melhem R, Arnoult C, Bourquard T, Jarlier M, Busson M, Laroche A, Cerutti M, Pugnière M, Ternant D, Gaborit N, Chardès T, Poupon A, Gouilleux-Gruart V, Pèlegrin A, Poul M A. MAbs. (2019) 11:593-605.
Peer D, Karp J M, Hong S, Farokhzad O C, Margalit R, Langer R. Nat Nanotechnol. (2007) 2:751-760.
Qian Z, LI H, SUN H, HO K. Pharmacol Rev. (2002) 54:561-587.
Richardson D R, Kalinowski D S, Lau S, Jansson P J, Lovejoy D B. Biochim. Biophys. Acta Gen Subj. (2009) 1790:702-717.
Shimosaki S, Nakahata S, Ichikawa T, Kitanaka A, Kameda T, Hidaka T, Kubuki Y, Kurosawa G, Zhang L, Sudo Y, Shimoda K, Morishita K. Biochem Biophys Res Commun. (2017) 485:144-151.
Sutherland R, Delia D, Schneider C, Newman R, Kemshead J, Greaves M. Proc Natl Acad Sci USA (1981) 78:4515-4519.
Trowbridge I S and Lopez F. Proc Natl Acad Sci USA. (1982) 79:1175-1179.
Ward J H. Invest Radiol. (1987) 22:74-83.
Winter & Milstein. Nature 1991; 349:293-299
Zhang L, Nomura F, Aikawa Y, Kurosawa Y, Morishita K, Sudo Y. Cancer Res. (2017) 77(13 Suppl):5586.

What is claimed is:

1. A binding agent targeting TfR1 including a light chain variable region wherein CDR1 to CDR3 have sequences identical to, respectively, SEQ ID NO: 5, SEQ ID NO: 6, and SEQ ID NO: 7, and a heavy chain variable region wherein CDR1 to CDR3 have sequences identical to, respectively, SEQ ID NO: 8, SEQ ID NO: 9, and SEQ ID NO: 10.

2. The binding agent of claim 1 wherein the binding agent is a monoclonal antibody.

3. The binding agent of claim 2 wherein the monoclonal antibody is a murine, humanized, chimeric, bispecific, or multispecific antibody.

4. The binding agent of claim 2 wherein the monoclonal antibody has an IgG1 heavy chain and κ light chain.

5. The binding agent of claim 1 wherein the binding agent is a Fab, Fab', F(ab')$_2$, rIgG, or Fv, fragment.

6. The binding agent of claim 1 wherein the binding agent is a scFv or a sc(Fv)$_2$.

7. The binding agent of claim 2 wherein the monoclonal antibody is class: IgD, IgE, IgG, IgA, or IgM, or a sub-class of one of said classes.

8. The binding agent of claim 7 wherein the monoclonal antibody sub-class is IgG1, IgG2, IgG3, IgG4, IgA1 or IgA2.

9. The binding agent of claim 7 wherein the monoclonal antibody has a κ light chain.

10. A binding agent targeting TfR1 having a heavy chain with a sequence identical to SEQ ID NO: 4 and a light chain with a sequence identical to SEQ ID NO: 2.

11. The binding agent of claim 10 conjugated to an anti-tumor agent.

12. The binding agent conjugate of claim 11 wherein the binding agent is a monoclonal antibody.

13. The binding agent conjugate of claim 12 wherein the monoclonal antibody is a murine, humanized, chimeric, bispecific, or multispecific antibody.

14. The binding agent conjugate of claim 12 wherein the monoclonal antibody has an IgG1 heavy chain and κ light chain.

15. The binding agent conjugate of claim 11 wherein the binding agent is a Fab, Fab', F(ab')$_2$, rIgG, or Fv fragment.

16. The binding agent conjugate of claim 11 wherein the binding agent is a scFv or a sc(Fv)$_2$.

17. The binding agent conjugate of claim 12 wherein the monoclonal antibody is class: IgD, IgE, IgG, IgA, or IgM, or a sub-class of one of said classes.

18. The binding agent conjugate of claim 17 wherein the monoclonal antibody sub-class is IgG1, IgG2, IgG3, IgG4, IgA1 or IgA2.

19. The binding agent of claim 1 conjugated to an anti-tumor agent.

* * * * *

UNITED STATES PATENT AND TRADEMARK OFFICE
CERTIFICATE OF CORRECTION

| | | |
|---|---|---|
| PATENT NO. | : 11,939,391 B2 | Page 1 of 1 |
| APPLICATION NO. | : 17/542948 | |
| DATED | : March 26, 2024 | |
| INVENTOR(S) | : Mason Lu and Qinhong Ma | |

It is certified that error appears in the above-identified patent and that said Letters Patent is hereby corrected as shown below:

On the Title Page

Item (73), add:
NORTHEAST PHARMACEUTICAL GROUP CO., LTD. of SHENYANG, CHINA

Signed and Sealed this
Sixteenth Day of September, 2025

Coke Morgan Stewart
*Acting Director of the United States Patent and Trademark Office*

SEQUENCE LISTING

<160> NUMBER OF SEQ ID NOS: 20

<210> SEQ ID NO 1
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

```
gacattgtga tgacacagtc tccatcctcc ctgactgtga cagcaggaga gaaggtcact    60
atgagctgca agtccagtca gagtctgtta aatagtggaa atcaaaagaa ctacttgacc   120
tggtaccagc agaaaccagg acagcctcct aaactgttga tctactgggc atccacttgg   180
gaatctaggg tccctgatca cttcacaggc agtggatctg gaacagattt cactctcacc   240
atcagcagtg tgcaggctga agacctggca gtctattact gtcagaatga ttatagttat   300
cctctcacgt tcggtgctgg gaccaagctg gagctgaaac gggctgatgc tgca         354
```

<210> SEQ ID NO 2
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

```
Ile Val Met Thr Gln Ser Pro Ser Ser Leu Thr Val Thr Ala Gly Glu
1               5                   10                  15

Lys Val Thr Met Ser Cys Lys Ser Ser Gln Ser Leu Leu Asn Ser Gly
            20                  25                  30

Asn Gln Lys Asn Tyr Leu Thr Trp Tyr Gln Gln Lys Pro Gly Gln Pro
        35                  40                  45

Pro Lys Leu Leu Ile Tyr Trp Ala Ser Thr Trp Glu Ser Arg Val Pro
    50                  55                  60

Asp His Phe Thr Gly Ser Gly Ser Gly Thr Asp Phe Thr Leu Thr Ile
65                  70                  75                  80

Ser Ser Val Gln Ala Glu Asp Leu Ala Val Tyr Tyr Cys Gln Asn Asp
                85                  90                  95

Tyr Ser Tyr Pro Leu Thr Phe Gly Ala Gly Thr Lys Leu Glu Leu Lys
            100                 105                 110

Arg Ala Asp Ala Ala
        115
```

<210> SEQ ID NO 3
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
gaggtccagc tgcagcagtc tggacctgag ctggtgaagc ctggggcttc agtgaggatt    60
tcctgcaaga cttctggcta caccttcaca aactactata cactggatga agcagagg    120
cctggacagg gacttgagtg gattggatgg atttatcctg agatggtaa ttctcattac   180
aatgagaagt tcaagggcaa gaccacactg actgcagaca atcctccag cacaggctac   240
```

```
atattgctca gcagcctgac ctctgaagac tctgcagtct atttctgtac aagagattat    300
gataactacg ggggatttgc ttactggggc caagggactc tggtcactgt ctct          354
```

```
<210> SEQ ID NO 4
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4
```

Glu Val Gln Leu Gln Gln Ser Gly Pro Glu Leu Val Lys Pro Gly Ala
1               5                   10                  15

Ser Val Arg Ile Ser Cys Lys Thr Ser Gly Tyr Thr Phe Thr Asn Tyr
            20                  25                  30

Tyr Ile His Trp Met Lys Gln Arg Pro Gly Gln Gly Leu Glu Trp Ile
        35                  40                  45

Gly Trp Ile Tyr Pro Gly Asp Gly Asn Ser His Tyr Asn Glu Lys Phe
    50                  55                  60

Lys Gly Lys Thr Thr Leu Thr Ala Asp Lys Ser Ser Ser Thr Gly Tyr
65                  70                  75                  80

Ile Leu Leu Ser Ser Leu Thr Ser Glu Asp Ser Ala Val Tyr Phe Cys
                85                  90                  95

Thr Arg Asp Tyr Asp Asn Tyr Gly Gly Phe Ala Tyr Trp Gly Gln Gly
            100                 105                 110

Thr Leu Val Thr Val Ser Ala
        115

```
<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5
```

Gln Ser Leu Leu Asn Ser Gly Asn Gln Lys Asn Tyr Leu Thr
1               5                   10

```
<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6
```

Trp Ala Ser Thr Trp Glu Ser Arg
1               5

```
<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7
```

Gln Asn Asp Tyr Ser Tyr Pro Leu Thr

-continued

```
<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Thr Ser Gly Tyr Thr Phe Thr Asn Tyr Tyr Ile His
1               5                   10

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Trp Ile Tyr Pro Gly Asp Gly Asn Ser His Tyr Asn Glu Lys Phe Lys
1               5                   10                  15

Gly

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Arg Asp Tyr Asp Asn Tyr Gly Gly Phe Ala Tyr
1               5                   10

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gaatgatgga tcaagctaga tcagc                                           25

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctcatggaag ctatgggtat cac                                             23

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 13
ctgctcactg gatggtggga agatgg                                              26

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
agctgggaag gtgtgcacac                                                     20

<210> SEQ ID NO 15
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
agcactagtg ccgccaccat ggaatcacag actcagg                                  37

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctgggcgccg ctacagtccg tttcagctcc agcttgg                                  37

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agctctagag ccgccaccat ggagacagac acactcctg                                39

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcctttggtg ctagcagaga cagtgaccag agtc                                     34

<210> SEQ ID NO 19
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 19
aactcctggg tggaccttgc gtgtttctgt tcccccctaa gc                    42

<210> SEQ ID NO 20
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aacacgcaag gtccacccag gagttcagga gcagggcaag g                     41
```